US008729201B2

(12) United States Patent
Fontaine et al.

(10) Patent No.: US 8,729,201 B2
(45) Date of Patent: May 20, 2014

(54) PROCESS FOR POLYMERIZING AN OLEFIN MONOMER AND CATALYST THEREFOR

(75) Inventors: Philip P. Fontaine, Manvel, TX (US); Roger L. Kuhlman, Lake Jackson, TX (US)

(73) Assignee: Dow Global Technologies LLC, Midland, MI (US)

(*) Notice: Subject to any disclaimer, the term of this patent is extended or adjusted under 35 U.S.C. 154(b) by 317 days.

(21) Appl. No.: 13/023,037

(22) Filed: Feb. 8, 2011

(65) Prior Publication Data

US 2011/0207903 A1  Aug. 25, 2011

Related U.S. Application Data

(60) Provisional application No. 61/306,153, filed on Feb. 19, 2010.

(51) Int. Cl.
*C08F 4/76* (2006.01)
*C08F 4/64* (2006.01)

(52) U.S. Cl.
USPC ............ 526/172; 526/160; 526/161; 526/170; 526/348

(58) Field of Classification Search
USPC ............. 556/51; 502/103; 526/172, 161, 160, 526/170
See application file for complete search history.

(56) References Cited

U.S. PATENT DOCUMENTS

| | | | |
|---|---|---|---|
| 5,637,660 A * | 6/1997 | Nagy et al. ............. | 526/160 |
| 6,096,676 A | 8/2000 | Murray | |
| 6,114,481 A | 9/2000 | McMeeking et al. | |
| 6,566,462 B2 | 5/2003 | Murray et al. | |
| 6,803,433 B2 | 10/2004 | Lee | |
| 6,919,413 B2 | 7/2005 | Murray | |
| 6,919,467 B2 | 7/2005 | Murray | |
| 6,939,969 B2 | 9/2005 | Peters et al. | |
| 7,067,686 B1 | 6/2006 | Rodriguez et al. | |
| 7,087,690 B2 | 8/2006 | Boussie et al. | |
| 7,199,255 B2 | 4/2007 | Murray et al. | |
| 7,355,089 B2 | 4/2008 | Chang et al. | |
| 7,858,718 B1 * | 12/2010 | Nagy et al. ............. | 526/172 |
| 2003/0166454 A1 | 9/2003 | Murray | |
| 2003/0204017 A1 | 10/2003 | Stevens et al. | |
| 2005/0187362 A1 | 8/2005 | Murray | |
| 2006/0199912 A1 | 9/2006 | Fuchs et al. | |
| 2008/0261804 A1 | 10/2008 | Roesky et al. | |
| 2009/0227626 A1 | 9/2009 | Deraeve et al. | |
| 2010/0048842 A1 | 2/2010 | Figueroa et al. | |
| 2011/0098431 A1 * | 4/2011 | Giesbrecht et al. ............ | 526/170 |

FOREIGN PATENT DOCUMENTS

| | | | |
|---|---|---|---|
| WO | 9623010 A2 | 8/1996 | |
| WO | 9633202 A2 | 10/1996 | |
| WO | 0140325 A1 | 6/2001 | |
| WO | 0202577 A1 | 1/2002 | |
| WO | 0238628 A2 | 5/2002 | |
| WO | 0246249 A2 | 6/2002 | |
| WO | 02079207 A2 | 10/2002 | |
| WO | 02092610 A1 | 11/2002 | |
| WO | 03051935 A1 | 6/2003 | |
| WO | 2004024740 A1 | 3/2004 | |
| WO | 2004074333 A2 | 9/2004 | |
| WO | 2005090425 A1 | 9/2005 | |
| WO | 2005090426 A1 | 9/2005 | |
| WO | 2005090427 A2 | 9/2005 | |
| WO | 2005123790 A1 | 12/2005 | |
| WO | 2008027283 A2 | 3/2008 | |

OTHER PUBLICATIONS

Shen et al., Dalton Trans., 2009, 9000-9009.*
Liu et al. Organometallics 2010, 29, 1916-1923.*
Fontaine et al. Organometallics 2012, 31, 6244-6251.*
Peters et al. Inorg. Chem. 2011, 40, 5083-5091.*
Oakes et al.; "The Surprisingly Beneficial Effect of Soft Donors on the Performance of Early Transition Metal Olefin Polymerization Catalysts."; Chemical Communications; the Royal Society of Chemistry; 2004; 2174-2175.
Adams et al., "Discovery and Evaluation of Highly Active Imidotitanium Ethylene Polymerisation Catalysts Using High Throughput Catalyst Screening", Chemical Communications, 2004, pp. 434-435, The Royal Society of Chemistry.
Al-Omari et al., "Bi-3H-diazirin-3-yls as Precursors of Highly Strained Cycloalkynes", Angewandte Chemie. Int. Ed., 2006, pp. 309-311, vol. 45.
Betley et al., "Group VIII Coordination Chemistry of a Pincer-Type Bis(8-quinolinyl)amido Ligand", Inorganic Chemistry, 2008, vol. 47 No. 24, pp. 11570-11582, American Chemical Society.
Bradley et al., "Metallo-Organic Compounds Containing Metal-Nitrogen Bonds Part IV. Some Bis-(Primary Amino)-Titanium Compounds", Canadian Journal of Chemistry, 1963, pp. 134-38, vol. 41.
Buu-Hoi et al., "Carcinogenic Nitrogen Compounds. XIX. Aptitude of Some Aminoquinolines for Cyclization", J. Chem. Soc. 1956, 2048-51.
Deraeve et al., "Preparation of new bis(8-aminoquinoline) ligands and comparison with bis(8-hydroxyquinoline) ligands on their ability to chelate Cu(II) and Zn(II)", European Journal of Inorganic Chemistry, 2008, vol. 36, pp. 5622-5631, Wiley-VCH Verlag GmbH & Co. KGaA.
De Waele et al., "Synthesis of Hafnium and Zirconium Imino-Amido Complexes from Bis-imine Ligands. A New Family of Olefin Polymerization Catalysts", Organometallics, 2007, pp. 3896-3899, vol. 26, American Chemical Society.
Gates et al., "Synthesis of Branched Polyethylene Using (α-Diimine)nickel(II) Catalysts: Influence of Temperature, Ethylene Pressure, and Ligand Structure on Polymer Properties", Macromolecules, 2000, pp. 2320-2334, vol. 33.
Kiesewetter et al., "Ethene/Norbornene Copolymerization with Palladium (II) α-Diimine Catalysts: From Ligand Screening to Discrete Catalyst Species", Chem. Eur. J., 2003, pp. 1750-1758, vol. 9 No. 8, Wiley-VCH Verlag GmbH & Co. KGaA, Weinheim.

(Continued)

*Primary Examiner* — Rip A. Lee

(57) ABSTRACT

The present invention generally relates to a process that polymerizes an olefin monomer, and a precatalyst and catalyst useful in such process.

10 Claims, 2 Drawing Sheets

(56) References Cited

OTHER PUBLICATIONS

Kim et al., "α-lminoenamido Ligands: A Novel Structure for Transition-Metal Activation", Organometallics, 2002, pp. 3082-3084, vol. 21.

Kim et al., "Activation of Enamido Zirconium Complexes for Ethylene Polymerization: Electrophilic Addition Versus Electrophilic Abstraction Reaction", Organometallics, 2003, pp. 1503-1511, vol. 22, American Chemical Society.

Kim et al., Activation of Enamido Zirconium Complexes for Olefin Polymerization: Electrophilic Addition Versus Electrophilic Abstraction Reaction. Polymer Preprints, 2003, vol. 44(I), pp. 990-991, American Chemical Society, Division of Polymer Chemistry.

Mashima et al. "Benzylation of α-Diimine Ligands Bound to Zirconium and Hafnium. A New Convenient Route to Olefin Polymerization Catalysts", Chemistry Letters, 2007, pp. 1420-1421, vol. 36 No. 12.

Nomura et al., "Nonbridged Half-Metallocenes Containing Anionic Ancillary Donor Ligands: New Promising Candidates as Catalysts for Precise Olefin Polymerization", Journal of Molecular Catalysis A: Chemical, 2007, vol. 267 pp. 1-29, Elsevier B.V.

Pappalardo et al., "New Neutral and Cationic Dialkylaluminium Complexes Bearing Imino-Amide or Imino-Phenoxide Ligands: Synthesis, Characterization and Reactivity With Olefins", Eur. J. Inorg. Chem. 2002, pp. 621-628.

Peters et al., "Pincer-Like Amido Complexes of Platinum, Palladium, and Nickel", Inorganic Chemistry, 2001, vol. 40 No. 20, pp. 5083-5091, American Chemical Society.

Shen et al., "Synthesis and characterization of organoaluminum compounds containing quinolin-8-amine derivatives and their catalytic behavior for ring-opening polymerization of $\epsilon$-caprolactone" Dalton Transactions, 2009, pp. 9000-9009, The Royal Society of Chemistry.

Wang et al., "Palladium-Catalyzed Microwave-Assisted Amination of 1-Bromonaphthalenes and 5- and 8- Bromoquinolines", Organic Letters, 2003, vol. 5 No. 6, pp., 897-900, American Chemical Society.

* cited by examiner

Scheme 1:

Scheme 2:

Scheme 3:

Scheme 4:

Option A: 1) Base
2) $M(Cl)_{n+1}$
3) X-Li or X-MgBr

Option B: 1) $M(NR^K R^L)_{n+1}$
2) X-Li or X-MgBr

Option C: organometallic $M(X)_{n+1}$

Option D: 1) $M(Cl)_{n+1}$
2) 3 mole equiv. X-Li or X-MgBr

PROCESS FOR POLYMERIZING AN OLEFIN MONOMER AND CATALYST THEREFOR

CROSS-REFERENCE TO RELATED APPLICATIONS

This application claims benefit from U.S. Provisional Patent Application No. 61/306,153, filed Feb. 19, 2010, the entire contents of which are hereby incorporated herein by reference.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention generally relates to a process that polymerizes an olefin monomer, and a precatalyst and catalyst useful in such process.

2. Description of Related Art

Polyolefins such as polyethylene polymer and poly(ethylene alpha-olefin) copolymers are widely used in industry. They are desirable for making, for example, containers, tubing, films and sheets for packaging, and synthetic lubricants, fibers, and pipes. Ethylene interpolymers are often blended or otherwise used in combination with other polymers to optimize the balance of properties for desired uses. Such blends may be generated by, for example, employing multiple reactors in series, or post-reactor by co-extrusion, elevated temperature mixing or kneading. Methods for generating such blends are discussed in more detail in, for example, US20060199912 A1.

A particularly valuable subtype of poly(ethylene alpha-olefin) copolymer is a poly(ethylene alpha-olefin) block copolymer or, simply, an olefin block copolymer (OBC). OBCs are characterized as having at least one so-called "hard segment" or block comprising residuals of ethylene monomer and at least one so-called "soft segment" or block comprising residuals of an alpha-olefin (also known as an alpha-olefin and 1-olefin) monomer. OBCs are available from The Dow Chemical Company, Midland, Mich., USA under the trade name INFUSE™ Olefin Block Copolymers. INFUSE™ Olefin Block Copolymers are useful in a variety of forms and applications such as, for example, those listed at www.dow.com/infuse. Preparation of an OBC can involve a process that, among other steps, polymerizes ethylene and the alpha-olefin using different catalysts to form the OBC.

U.S. Pat. No. 6,566,462 B2 mentions, among other things, a certain process to polymerize olefins comprising reacting olefins with a catalyst system comprising an activator, a metallocene and a second metal compound based on bidentate ligands containing heterocycle moieties, and preferably pyridine or quinoline moieties. U.S. Pat. No. 6,566,462 B2 also mentions a certain composition comprising a metallocene and a second metal compound. U.S. Pat. No. 6,566,462 B2 does not mention or disclose any species of the second metal compound wherein the heterocycle moiety is a quinoline moiety.

U.S. Pat. No. 7,199,255 B2 mentions, among other things, a catalyst precursor, a catalyst system comprising the precursor, and an olefin polymerization method using the catalyst system. U.S. Pat. No. 7,199,255 B2 does not mention or disclose any species of the second metal compound wherein the catalyst precursor contains a quinoline moiety.

WO 02/079207 A2 mentions, among other things, an amido ligand and its synthesis, and use of the amide ligand in a variety of metal complexes, and transition metals in particular. WO 02/079207 A2 also mentions that amido ligand transition metal complexes are expected to find utility as catalysts in numerous stoichiometric and catalytic transformations such as, by way of example and not limitation, hydroamination, olefin hydration, alkane oxidation, dioxygen activation and subsequent olefin epoxidation, dinitrogen activation/reduction/functionalization, olefin polymerization/copolymerization/living polymerization, catalytic C-E bond formation (where E is C, N, O, S, Si, H, and so forth), as well as Heck, Suzuki, and Sonagoshira coupling reactions. WO 02/079207 A2 does not mention or disclose any species of the amido ligand transition metal complex wherein the transition metal is a metal of Group 3, 4, 5, or 6 of the Periodic Table of the Elements.

Shen M., et al., *Synthesis and characterization of organoaluminum compounds containing quinolin-8-amine derivatives and their catalytic behaviour for ring-opening polymerization of ε-caprolactone*, Dalton Transactions, 2009: 9000-9009, mention certain organoaluminum compounds containing certain 2-substituted, N-substituted quinolin-8-amine derived ligands.

Chemical industry desires new processes and catalysts for polymerizing olefin monomers.

BRIEF SUMMARY OF THE INVENTION

In a first embodiment, the present invention is a process for polymerizing an olefin monomer, the process comprising a step of contacting together a catalytic amount of a catalyst comprising a mixture or reaction product of ingredients (a) and (b), wherein ingredient (a) comprises a metal-ligand complex and ingredient (b) comprises an activating co-catalyst; and an olefin monomer as ingredient (c); the ingredient (a) being one or more metal-ligand complexes (also referred to herein as precatalysts) of formula (I):

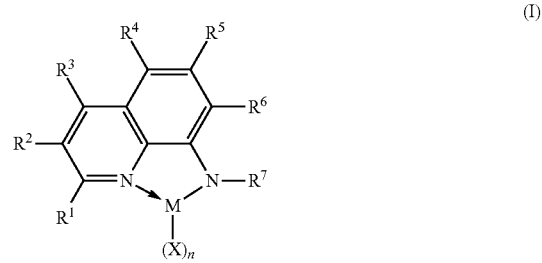

wherein:
M is a metal of any one of Groups 3, 4, 5, and 6 of the Periodic Table of the Elements, the metal being in a formal oxidation state of +2, +3, +4, +5, or +6;
n is an integer of from 1 to 5;

Each X independently is a monodentate ligand that is neutral, monoanionic, or dianionic; or two X are taken together to form a bidentate ligand that is neutral, monoanionic, or dianionic;

X and n are chosen in such a way that the metal-ligand complex of formula (I) is, in aggregate, neutral;

Each of $R^1$ to $R^6$ independently is a hydrogen atom, $(C_1\text{-}C_{40})$hydrocarbyl, $(C_1\text{-}C_{40})$heterohydrocarbyl, $(C_1\text{-}C_{40})$hydrocarbyl-O—, or halogen atom;

$R^7$ independently is a $(C_1\text{-}C_{40})$hydrocarbyl or $(C_1\text{-}C_{40})$heterohydrocarbyl;

Or one X, when a monodentate ligand, is taken together with any one of $R^1$ to $R^7$ in such a way so that the metal-ligand complex of formula (I) contains a tridentate ligand (such that the tridentate ligand is bonded to M via the X, quinoline ring nitrogen atom, and nitrogen atom bearing $R^7$);

Each of the aforementioned hydrocarbyl (e.g., $(C_1\text{-}C_{40})$hydrocarbyl and $(C_1\text{-}C_{40})$hydrocarbyl of $(C_1\text{-}C_{40})$hydrocarbyl-O—) and heterohydrocarbyl independently is unsubstituted or substituted with one or more substituents $R^S$; and Each $R^S$ independently is a halogen atom, polyfluoro, perfluoro, unsubstituted $(C_1\text{-}C_{18})$alkyl, $F_3C$—, $FCH_2O$—, $F_2HCO$—, $F_3CO$—, $R_3Si$—, $RO$—, $RS$—, $RS(O)$—, $RS(O)_2$—, $R_2P$—, $R_2N$—, $R_2C=N$—, $NC$—, $RC(O)O$—, $ROC(O)$—, $RC(O)N(R)$—, or $R_2NC(O)$—, wherein each R independently is an unsubstituted $(C_1\text{-}C_{18})$alkyl; and the ingredient (b) being one or more activating co-catalysts, or a reaction product thereof, wherein the ratio of total number of moles of the one or more metal-ligand complexes of formula (I) to total number of moles of the one or more activating co-catalysts is from 1:10,000 to 100:1; wherein the contacting step is performed under olefin polymerizing conditions (described later) and prepares a polyolefin.

In a second embodiment the present invention is the metal-ligand complex of formula (I).

In a third embodiment the present invention is a catalyst comprising or prepared from the one or more metal-ligand complexes of formula (I) and one or more activating co-catalysts, or a reaction product thereof, wherein the ratio of total number of moles of the one or more metal-ligand complexes of formula (I) to total number of moles of the one or more activating co-catalysts is from 1:10,000 to 100:1.

The invention also contemplates a process for preparing the metal-ligand complex of formula (I) by reacting a ligand of formula (Q):

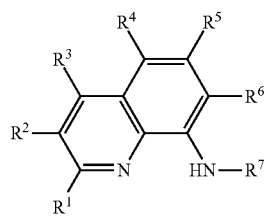

(Q)

or a Group 1 or 2 metal salt of the ligand of formula (Q), wherein the metal of the Group 1 or 2 metal salt is a cation of any one of the metals of Groups 1 and 2 of the Periodic Table of the Elements, with a source or sources of M and X (e.g., a salt of formula $M(X)_{n+1}$) in such a way so as to prepare the metal-ligand complex of formula (I), wherein the metal-ligand complex of formula (I), M, X, and $R^1$ to $R^7$ are as defined in the first embodiment.

The invention also contemplates a process for preparing the ligand of formula (Q), and intermediates in the preparation thereof.

The ligand of formula (Q) is useful in the process of preparing the metal-ligand complex of formula (I), which in turn is useful in the process of preparing the invention catalyst as described herein.

In another embodiment the present invention is a ligand of formula (Qp):

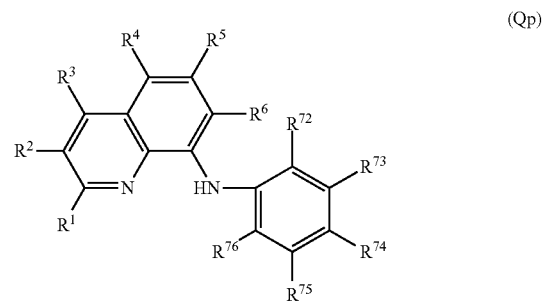

(Qp)

or a Group 1 or 2 metal salt thereof, wherein the Group 1 or 2 metal of the Group 1 or 2 metal salt is a cation of any one of the metals of Groups 1 and 2 of the Periodic Table of the Elements;

Each of $R^1$ to $R^6$ independently is a hydrogen atom, $(C_1\text{-}C_{40})$hydrocarbyl, $(C_1\text{-}C_{40})$heterohydrocarbyl, $(C_1\text{-}C_{40})$hydrocarbyl-O—, or halogen atom;

At least one of $R^{72}$ and $R^{76}$ independently is a $(C_1\text{-}C_{40})$alkyl and each of the remainder of $R^{72}$ to $R^{76}$ independently is a hydrogen atom or $R^S$, wherein $R^S$ is as defined previously;

Each of the aforementioned hydrocarbyl (e.g., $(C_1\text{-}C_{40})$hydrocarbyl) and heterohydrocarbyl independently is unsubstituted or substituted with one or more substituents $R^S$; and Each $R^S$ independently is a halogen atom, polyfluoro, perfluoro, unsubstituted $(C_1\text{-}C_{18})$alkyl, $F_3C$—, $FCH_2O$—, $F_2HCO$—, $F_3CO$—, $R_3Si$—, $RO$—, $RS$—, $RS(O)$—, $RS(O)_2$—, $R_2P$—, $R_2N$—, $R_2C=N$—, $NC$—, $RC(O)O$—, $ROC(O)$—, $RC(O)N(R)$—, or $R_2NC(O)$—, wherein each R independently is an unsubstituted $(C_1\text{-}C_{18})$alkyl.

The metal-ligand complex(es) of formula (I) and catalyst(s) prepared therefrom with the one or more activating co-catalysts are useful in the process of the first embodiment. As can be illustrated later, the invention process is characterizable by one or more activities of the catalyst(s), one or more properties of the polyolefin prepared thereby, or a combination thereof.

Accordingly, the present invention also contemplates novel polyolefins prepared by the process of the first embodiment. Examples of polyolefins that can be prepared by the invention process are a polyethylene, poly(alpha-olefin), polystyrene, and poly(ethylene alpha-olefin) copolymer, including poly(ethylene alpha-olefin) block copolymer. The term "poly(ethylene alpha-olefin) block copolymer" is used interchangeably herein with the terms "olefin block copolymer," "OBC," "ethylene/α-olefin block interpolymer," and "ethylene/α-olefin block copolymer". The terms "alpha-olefin" and "α-olefin" are used interchangeably herein. The term "ethylene" means ethene, i.e., $H_2C=CH_2$.

The polyolefins prepared by the process of the first embodiment are useful in numerous applications such as, for example, synthetic lubricants, films, fibers, pipes, and elastic films for hygiene applications (e.g., for diaper covers); flexible molded goods for appliances, tools, consumer goods (e.g., toothbrush handles), sporting goods, building and construction components, automotive parts, and medical applications (e.g., medical devices); flexible gaskets and profiles for appliance (e.g., refrigerator door gaskets and profiles), building and construction, and automotive applications; adhesives for packaging (e.g., for use in manufacturing corrugated cardboard boxes), hygiene applications, tapes, and labels; and foams for sporting goods (e.g., foam mats), packaging, consumer goods, and automotive applications.

Additional embodiments are described in the remainder of the specification, including the claims.

BRIEF DESCRIPTION OF THE DRAWING(S)

Some embodiments of the present invention are described herein in relation to the accompanying drawing(s), which will at least assist in illustrating various features of the embodiments.

DETAILED DESCRIPTION OF THE INVENTION

Figure 1:
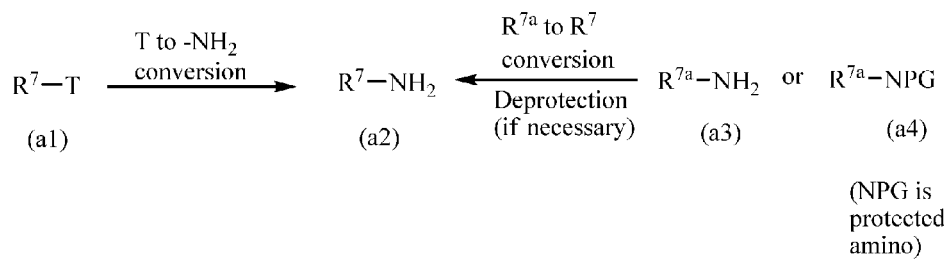
FIG. 1 shows an illustrative procedure of Scheme 1 for preparing a first primary intermediate useful in a convergent synthesis of the ligand of formula (Q).

For purposes of United States patent practice and other patent practices allowing incorporation of subject matter by reference, the entire contents—unless otherwise indicated—of each U.S. patent, U.S. patent application, U.S. patent application publication, PCT international patent application and WO publication equivalent thereof, referenced in the instant Summary or Detailed Description of the Invention are hereby incorporated by reference. In an event where there is a conflict between what is written in the present specification and what is written in a patent, patent application, or patent application publication, or a portion thereof that is incorporated by reference, what is written in the present specification controls.

In the present application, any lower limit of a range of numbers, or any preferred lower limit of the range, may be combined with any upper limit of the range, or any preferred upper limit of the range, to define a preferred aspect or embodiment of the range. Each range of numbers includes all numbers, both rational and irrational numbers, subsumed within that range (e.g., the range from about 1 to about 5 includes, for example, 1, 1.5, 2, 2.75, 3, 3.80, 4, and 5).

Certain unsubstituted chemical groups are described herein as having a maximum number of 40 carbon atoms (e.g., $(C_1-C_{40})$hydrocarbyl and $(C_1-C_{40})$heterohydrocarbyl). These include substituent groups (e.g., R groups) and olefin monomers where number of carbon atoms is not critical. Forty carbon atoms in such unsubstituted chemical groups is a practical upper limit; nevertheless in some embodiments the invention contemplates such unsubstituted chemical groups having a maximum number of carbon atoms that is higher than 40 (e.g., 100, 1000, or more).

The word "optionally" means "with or without." For example, "optionally, an additive" means with or without an additive.

In an event where there is a conflict between a compound name and its structure, the structure controls.

In an event where there is a conflict between a unit value that is recited without parentheses, e.g., 2 inches, and a corresponding unit value that is parenthetically recited, e.g., (5 centimeters), the unit value recited without parentheses controls.

As used herein, "a," "an," "the," "at least one," and "one or more" are used interchangeably. In any aspect or embodiment of the instant invention described herein, the term "about" in a phrase referring to a numerical value may be deleted from the phrase to give another aspect or embodiment of the instant invention. In the former aspects or embodiments employing the term "about," meaning of "about" can be construed from context of its use. Preferably "about" means from 90 percent to 100 percent of the numerical value, from 100 percent to 110 percent of the numerical value, or from 90 percent to 110 percent of the numerical value. In any aspect or embodiment of the instant invention described herein, the open-ended terms "comprising," "comprises," and the like (which are synonymous with "including," "having," and "characterized by") may be replaced by the respective partially closed phrases "consisting essentially of," "consists essentially of," and the like or the respective closed phrases "consisting of," "consists of," and the like to give another aspect or embodiment of the instant invention. The term "characterizable" is open-ended and means distinguishable. In the present application, when referring to a preceding list of elements (e.g., ingredients), the phrases "mixture thereof," "combination thereof," and the like mean any two or more, including all, of the listed elements. The term "or" used in a listing of members, unless stated otherwise, refers to the listed members individually as well as in any combination, and supports additional embodiments reciting any one of the individual members (e.g., in an embodiment reciting the phrase "10 percent or more," the "or" supports another embodiment reciting "10 percent" and still another embodiment reciting "more than 10 percent."). The term "plurality" means two or more, wherein each plurality is independently selected unless indicated otherwise. The term "independently" means separately without regard for another. The terms "first," "second," et cetera serve as a convenient means of distinguishing between two or more elements or limitations (e.g., a first chair and a second chair) and do not imply quantity or order unless specifically so indicated. The symbols "≤" and "≥" respectively mean less than or equal to and greater than or equal to. The symbols "<" and ">" respectively mean less than and greater than.

Unless otherwise noted, the phrase "Periodic Table of the Elements" refers to the official periodic table, version dated Jun. 22, 2007, published by the International Union of Pure and Applied Chemistry (IUPAC). Also any references to a Group or Groups shall be to the Group or Groups reflected in this Periodic Table of the Elements.

When used to describe a chemical group (e.g., $(C_1-C_{40})$alkyl), the parenthetical expression of the form "$(C_x-C_y)$," means that the unsubstituted version of the chemical group comprises from a number x carbon atoms to a number y carbon atoms, wherein each x and y independently is an integer as described for the chemical group. Thus, for example, an unsubstituted $(C_1-C_{40})$alkyl contains from 1 to 40 carbon atoms. When one or more substituents on the chemical group contain one or more carbon atoms, the substituted $(C_x-C_y)$ chemical group may or may not comprise more than y total carbon atoms; i.e., the maximum total number of carbon atoms of the substituted $(C_x-C_y)$ chemical group would be equal to y plus the sum of the number of carbon atoms of each of the substituent(s). Any atom of a chemical group that is not specified herein is understood to be a hydrogen atom.

In some embodiments, an invention compound (e.g., the metal-ligand complex of formula (I)) contains one or more of the substituents $R^S$. Preferably there are not more than 20 $R^S$, more preferably not more than 10 $R^S$, and still more preferably not more than 5 $R^S$ in the compound. Where the invention compound contains two or more substituents $R^S$, each $R^S$ independently is bonded to a same or different substituted chemical group.

In some embodiments, at least one $R^S$ is polyfluoro or perfluoro. For present purposes "polyfluoro" and "perfluoro" each count as one $R^S$ substituent. The term "poly" as in "polyfluoro" means that two or more H, but not all H, bonded to carbon atoms of a corresponding unsubstituted chemical group are replaced by a fluoro in the substituted chemical group. The term "per" as in "perfluoro" means each H bonded to carbon atoms of a corresponding unsubstituted chemical group is replaced by a fluoro in the substituted chemical group.

As used herein, the term "$(C_1-C_{40})$hydrocarbyl" means a hydrocarbon radical of from 1 to 40 carbon atoms and the term "$(C_1-C_{40})$hydrocarbylene" means a hydrocarbon diradical of from 1 to 40 carbon atoms, wherein each hydrocarbon radical and diradical independently is aromatic or non-aromatic, saturated or unsaturated, straight chain or branched chain, cyclic (including mono- and poly-cyclic, fused and non-fused polycyclic) or acyclic, or a combination of two or more thereof; and each hydrocarbon radical and diradical is the same as or different from another hydrocarbon radical and diradical, respectively, and independently is unsubstituted or substituted by one or more $R^S$.

Preferably, a $(C_1-C_{40})$hydrocarbyl independently is an unsubstituted or substituted $(C_1-C_{40})$alkyl, $(C_3-C_{40})$cycloalkyl, $(C_3-C_{20})$cycloalkyl-$(C_1-C_{20})$alkylene, $(C_6-C_{40})$aryl, or $(C_6-C_{20})$aryl-$(C_1-C_{20})$alkylene. More preferably, a $(C_1-C_{40})$hydrocarbyl independently is an unsubstituted or substituted $(C_1-C_{20})$hydrocarbyl, e.g., $(C_1-C_{20})$alkyl, $(C_3-C_{20})$cycloalkyl, $(C_3-C_{10})$cycloalkyl-$(C_1-C_{10})$alkylene, $(C_6-C_{20})$aryl, or $(C_6-C_{18})$aryl-$(C_1-C_{10})$alkylene. Still more preferably, a $(C_1-C_{40})$hydrocarbyl independently is an unsubstituted or substituted $(C_1-C_{18})$hydrocarbyl, e.g., $(C_1-C_{18})$alkyl, $(C_3-C_{18})$cycloalkyl, $(C_3-C_{12})$cycloalkyl-$(C_1-C_6)$alkylene, $(C_6-C_{18})$aryl, or $(C_6-C_{12})$aryl-$(C_1-C_6)$alkylene. Preferably, any $(C_3-C_{18})$cycloalkyl independently is an unsubstituted or substituted $(C_3-C_{10})$cycloalkyl.

The term "$(C_1-C_{40})$alkyl" means a saturated straight or branched hydrocarbon radical of from 1 to 40 carbon atoms that is unsubstituted or substituted by one or more $R^S$. Examples of unsubstituted $(C_1-C_{40})$alkyl are unsubstituted $(C_1-C_{20})$alkyl; unsubstituted $(C_1-C_{10})$alkyl; unsubstituted $(C_1-C_5)$alkyl; methyl; ethyl; 1-propyl; 2-propyl; 1-butyl; 2-butyl; 2-methylpropyl; 1,1-dimethylethyl; 1-pentyl; 1-hexyl; 1-heptyl; 1-nonyl; and 1-decyl. Examples of substituted $(C_1-C_{40})$alkyl are substituted $(C_1-C_{20})$alkyl, substituted $(C_1-C_{10})$alkyl, trifluoromethyl, and $(C_{45})$alkyl. Preferably, each $(C_1-C_5)$alkyl independently is methyl, trifluoromethyl, ethyl, 1-propyl, or 2-methylethyl.

The term "$(C_1-C_{20})$alkylene" means a saturated straight or branched chain diradical of from 1 to 20 carbon atoms that is unsubstituted or substituted by one or more $R^S$. Preferably, $(C_1-C_{20})$alkylene, together with atoms of formula (I) through which the $(C_1-C_{20})$alkylene is bonded, comprise a 5- or 6-membered ring. Examples of unsubstituted $(C_1-C_{20})$alkylene are unsubstituted $(C_1-C_{10})$alkylene, including unsubstituted 1,2-$(C_1-C_{10})$alkylene; —CH$_2$—, —CH$_2$CH$_2$—, —(CH$_2$)$_3$—,

—(CH$_2$)$_4$—, —(CH$_2$)$_5$—, —(C$_2$)$_6$—, —(CH$_2$)$_7$—, —(CH$_2$)$_8$—, and —(CH$_2$)$_4$C(H)(CH$_3$)—. Examples of substituted $(C_1-C_{20})$alkylene are substituted $(C_1-C_{10})$alkylene, —CF$_2$—, —C(O)—, and —(CH$_2$)$_{14}$C(CH$_3$)$_2$(CH$_2$)$_5$— (i.e., a 6,6-dimethyl substituted normal-1,20-eicosylene).

The term "$(C_6-C_{40})$aryl" means an unsubstituted or substituted (by one or more $R^S$) mono-, bi- or tricyclic aromatic hydrocarbon radical of from 6 to 40 total carbon atoms, of which at least from 6 to 14 carbon atoms are ring carbon atoms, and the mono-, bi- or tricyclic radical comprises 1, 2 or 3 rings (first, second, and third rings, respectively), wherein any second or third ring independently is fused or non-fused to a first ring or each other, and the first ring is aromatic and, preferably, at least one of any second or third rings is aromatic. Examples of unsubstituted $(C_6-C_{40})$aryl are unsubstituted $(C_6-C_{20})$aryl; unsubstituted $(C_6-C_{18})$aryl; unsubstituted $(C_6-C_{12})$aryl; phenyl; fluorenyl; tetrahydrofluorenyl; indacenyl; hexahydroindacenyl; indenyl; dihydroindenyl; naphthyl; tetrahydronaphthyl; and phenanthrenyl. Examples of substituted $(C_6-C_{40})$aryl are substituted $(C_6-C_{20})$aryl; substituted $(C_6-C_{18})$aryl; substituted $(C_6-C_{12})$aryl; 2-$(C_1-C_5)$alkyl-phenyl; 2,4-bis$(C_1-C_5)$alkyl-phenyl; 2,4-bis[$(C_{20})$alkyl]-phenyl; polyfluorophenyl; pentafluorophenyl; and fluoren-9-one-1-yl. A preferred substituted $(C_6-C_{12})$aryl is a substituted $(C_6)$aryl, more preferably 2,6-bis(1-methylethyl)phenyl.

The term "$(C_3-C_{40})$cycloalkyl" means a saturated cyclic hydrocarbon radical of from 3 to 40 carbon atoms that is unsubstituted or substituted by one or more $R^S$. Examples of unsubstituted $(C_3-C_{40})$cycloalkyl are unsubstituted $(C_3-C_{20})$cycloalkyl, unsubstituted $(C_3-C_{10})$cycloalkyl, cyclopropyl, cyclobutyl, cyclopentyl, cyclohexyl, cycloheptyl, cyclooctyl, cyclononyl, and cyclodecyl. Examples of substituted $(C_3-C_{40})$cycloalkyl are substituted $(C_3-C_{20})$cycloalkyl, substituted $(C_3-C_{10})$cycloalkyl, cyclopentanon-2-yl, and 1-fluorocyclohexyl.

Examples of $(C_1-C_{40})$hydrocarbylene are unsubstituted or substituted $(C_6-C_{40})$arylene, $(C_3-C_{40})$cycloalkylene, and $(C_1-C_{40})$alkylene (e.g., $(C_1-C_{20})$alkylene). In some embodiments, the diradicals are on adjacent carbon atoms (i.e., 1,2-diradicals), or spaced apart by one, two, or more intervening carbon atoms (e.g., respective 1,3-diradicals, 1,4-diradicals, etc.). Preferred is a 1,2-, 1,3-, 1,4-, or an alpha,omega-diradical (i.e., having maximum spacing between the radical carbons), more preferably a 1,2-diradical. More preferred are 1,2-diradical versions of $(C_6-C_{18})$arylene, $(C_3-C_{20})$cycloalkylene, and $(C_2-C_{20})$alkylene.

The term "$(C_1-C_{40})$heterohydrocarbyl" means a heterohydrocarbon radical of from 1 to 40 carbon atoms and one or more heteroatoms N (when comprising —N=, as in certain nitrogen containing heteroaryl groups, e.g., an isoxazolyl); O; S; S(O); S(O)$_2$; Si(R$^C$)$_2$; P(R$^P$); and N(R$^N$), wherein independently each R$^C$ is unsubstituted $(C_1-C_{18})$hydrocarbyl, each R$^P$ is unsubstituted $(C_1-C_{18})$hydrocarbyl; and each R$^N$ is unsubstituted $(C_1-C_{18})$hydrocarbyl. The term "$(C_1-C_{40})$heterohydrocarbylene" means a heterohydrocarbon diradical of from 1 to 40 carbon atoms and one or more heteroatoms Si(R$^C$)$_2$, P(R$^P$), N(R$^N$), N, O, S, S(O), and S(O)$_2$ as defined above. The heterohydrocarbon radical and each of the heterohydrocarbon diradicals independently are on a carbon atom or heteroatom thereof. Each heterohydrocarbon radical and diradical independently is unsubstituted or substituted (by one or more $R^S$), aromatic or non-aromatic, saturated or unsaturated, straight chain or branched chain, cyclic (including mono- and poly-cyclic, fused and non-fused polycyclic) or acyclic, or a combination of two or more thereof; and each heterohydrocarbon is the same as or different from another heterohydrocarbon radical and diradical, respectively.

Preferably, a $(C_1-C_{40})$heterohydrocarbyl independently is unsubstituted or substituted $(C_1-C_{40})$heteroalkyl, $(C_2-C_{40})$heterocycloalkyl, $(C_2-C_{40})$heterocycloalkyl-$(C_1-C_{20})$alkylene, $(C_3-C_{40})$cycloalkyl-$(C_1-C_{20})$heteroalkylene, $(C_2-C_{40})$heterocycloalkyl-$(C_1-C_{20})$heteroalkylene, $(C_1-C_{40})$heteroaryl, $(C_1-C_{20})$heteroaryl-$(C_1-C_{20})$alkylene, $(C_6-C_{20})$aryl-$(C_1-C_{20})$heteroalkylene, or $(C_1-C_{20})$heteroaryl-$(C_1-C_{20})$heteroalkylene. More preferably, a $(C_1-C_{40})$heterohydrocarbyl independently is unsubstituted or substituted $(C_1-C_{20})$heterohydrocarbyl, e.g., $(C_1-C_{20})$heteroalkyl, $(C_2-C_{20})$heterocycloalkyl, $(C_2-C_{20})$heterocycloalkyl-$(C_1-C_{20})$alkylene, $(C_3-C_{20})$cycloalkyl-$(C_1-C_{20})$heteroalkylene, $(C_2-C_{20})$heterocycloalkyl-$(C_1-C_{20})$heteroalkylene, $(C_1-C_{20})$heteroaryl, $(C_1-C_{20})$heteroaryl-$(C_1-C_{20})$alkylene, $(C_6-C_{20})$aryl-$(C_1-C_{20})$heteroalkylene, or $(C_1-C_{20})$heteroaryl-$(C_1-C_{20})$heteroalkylene. Still more preferably, a $(C_1-C_{40})$heterohydrocarbyl independently is unsubstituted or substituted $(C_1-C_{18})$heterohydrocarbyl, e.g., $(C_1-C_{18})$heteroalkyl, $(C_2-C_{18})$heterocycloalkyl, $(C_2-C_{12})$heterocycloalkyl-$(C_1-C_6)$alkylene, $(C_3-C_{12})$cycloalkyl-$(C_1-C_6)$heteroalkylene, $(C_2-C_{12})$heterocycloalkyl-$(C_1-C_6)$heteroalkylene, $(C_1-C_{12})$heteroaryl, $(C_1-C_{12})$heteroaryl-$(C_1-C_6)$alkylene, $(C_6-C_{18})$aryl-$(C_1-C_6)$heteroalkylene, or $(C_1-C_{12})$heteroaryl-$(C_1-C_6)$heteroalkylene. Preferably, any $(C_2-C_{18})$heterocycloalkyl independently is unsubstituted or substituted $(C_2-C_9)$heterocycloalkyl.

Examples of $(C_1-C_{40})$heteroalkyl and $(C_1-C_{20})$heteroalkylene are saturated straight or branched chain radical or diradical, respectively, of from 1 to 40 or 1 to 20 carbon atoms, respectively, and one or more of the heteroatoms $Si(R^C)_2$, $P(R^P)$, $N(R^N)$, N, O, S, S(O), and $S(O)_2$ as defined above, wherein the $(C_1-C_{40})$heteroalkyl and $(C_1-C_{20})$heteroalkylene independently are unsubstituted or substituted by one or more $R^S$.

Examples of unsubstituted $(C_2-C_{40})$heterocycloalkyl are unsubstituted $(C_2-C_{20})$heterocycloalkyl, unsubstituted $(C_2-C_{10})$heterocycloalkyl, aziridin-1-yl, oxetan-2-yl, tetrahydrofuran-3-yl, pyrrolidin-1-yl, tetrahydrothiophen-S,S-dioxide-2-yl, morpholin-4-yl, 1,4-dioxan-2-yl, hexahydroazepin-4-yl, 3-oxa-cyclooctyl, 5-thia-cyclononyl, and 2-aza-cyclodecyl.

Examples of unsubstituted $(C_1-C_{40})$heteroaryl are unsubstituted $(C_1-C_{20})$heteroaryl, unsubstituted $(C_1-C_{10})$heteroaryl, pyrrol-1-yl; pyrrol-2-yl; furan-3-yl; thiophen-2-yl; pyrazol-1-yl; isoxazol-2-yl; isothiazol-5-yl; imidazol-2-yl; oxazol-4-yl; thiazol-2-yl; 1,2,4-triazol-1-yl; 1,3,4-oxadiazol-2-yl; 1,3,4-thiadiazol-2-yl; tetrazol-1-yl; tetrazol-2-yl; tetrazol-5-yl; pyridine-2-yl; pyrimidin-2-yl; pyrazin-2-yl; indol-1-yl; benzimidazole-1-yl; quinolin-2-yl; and isoquinolin-1-yl.

The term "halogen atom" means a fluoro (F), chloro (Cl), bromo (Br), or iodo (I) radical. Preferably, halogen atom is fluoro or chloro, more preferably fluoro.

Preferably, there are no O—O, S—S, or O—S bonds, other than O—S bonds in an S(O) or $S(O)_2$ diradical functional group, in the metal-ligand complex of formula (I).

Preferably, each substituted $(C_1-C_{40})$hydrocarbyl excludes and is different than unsubstituted or substituted $(C_1-C_{40})$heterohydrocarbyl; preferably, each substituted $(C_1-C_{40})$hydrocarbylene excludes and is different than unsubstituted or substituted $(C_1-C_{40})$heterohydrocarbylene; and more preferably a combination thereof.

The term "saturated" means lacking carbon-carbon double bonds, carbon-carbon triple bonds, and (in heteroatom-containing groups) carbon-nitrogen, carbon-phosphorous, and carbon-silicon double bonds. Where a saturated chemical group is substituted by one or more substituents $R^S$, one or more double and/or triple bonds optionally may or may not be present in the substituents $R^S$. The term "unsaturated" means containing one or more carbon-carbon double bonds, carbon-carbon triple bonds, and (in heteroatom-containing groups) carbon-nitrogen, carbon-phosphorous, and carbon-silicon double bonds, not including any such double bonds that may or may not be present in the substituents $R^S$ or in (hetero) aromatic rings, if any.

Some embodiments contemplate a trivalent or tetravalent analog of a diradical group. As applied to the diradical group, the term "trivalent or tetravalent analog" respectively means a triradical or tetraradical that is formally derived by abstracting one or two hydrogen atoms, respectively, from the diradical group. Preferably, each abstracted hydrogen atom independently is taken from a C—H functionality. A trivalent analog is preferred over a tetravalent analog.

The term "solvent" means a liquid, preferably aprotic, that is compatible with the invention process. Suitable solvents include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; benzene and $(C_1-C_5)$alkyl-substituted benzenes such as toluene and xylene; $(C_1-C_5)$alkyl-O—$(C_1-C_5)$alkyl; $(C_4-C_5)$heterocycloalkyl such as tetrahydrofuran, tetrahydropyran, and 1,4-dioxane; $(C_1-C_5)$alkyl ethers of (poly)alkylene glycols; and mixtures of the foregoing.

As mentioned previously, another aspect of the present invention is a polyolefin prepared according to a process of the first embodiment. In some embodiments, polymerizable olefins useful in the invention processes are $(C_2-C_{40})$hydrocarbons consisting of carbon and hydrogen atoms and containing at least 1 and preferably no more than 3, and more preferably no more than 2 carbon-carbon double bonds. In some embodiments, from 1 to 4 hydrogen atoms of the $(C_2-C_{40})$hydrocarbon are replaced, each by a halogen atom, preferably fluoro or chloro to give halogen atom-substituted $(C_2-C_{40})$hydrocarbons. The $(C_2-C_{40})$hydrocarbons (not halogen atom-substituted) are preferred. Preferred polymerizable olefins (i.e., olefin monomers) useful for making the polyolefins are ethylene and polymerizable $(C_3-C_{40})$olefins. The $(C_3-C_{40})$olefins include an alpha-olefin, a cyclic olefin, styrene, and a cyclic or acyclic diene. Preferably, the alpha-olefin comprises the $(C_3-C_{40})$alpha-olefin, more preferably a branched chain $(C_3-C_{40})$alpha-olefin, still more preferably a linear-chain $(C_3-C_{40})$alpha-olefin, even more preferably a linear chain $(C_3-C_{40})$alpha-olefin of formula (A): $CH_2=CH_2-(CH_2)_zCH_3$ (A), wherein z is an integer of from 0 to 40, and yet even more preferably a linear-chain $(C_3-C_{40})$ alpha-olefin that is 1-propene, 1-butene, 1-pentene, 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, or a linear-chain $(C_{20}-C_{24})$alpha-olefin. Preferably the cyclic olefin is a ($C_3$-$C_{40}$)cyclic olefin. Preferably, the cyclic or acyclic diene is a ($C_4$-$C_{40}$)diene, preferably an acyclic diene, more preferably an acyclic conjugated ($C_4$-$C_{40}$)diene, more preferably an acyclic 1,3-conjugated ($C_4$-$C_{40}$)diene, and still more preferably 1,3-butadiene.

Polyolefins that can be made by an invention process include, for example, polyethylene and interpolymers that comprise residuals of ethylene and one or more polymerizable ($C_3$-$C_{40}$)olefins. Preferred homopolymers are polyethylene, polypropylene, and polybutylene. Preferred interpolymers are those prepared by co-polymerizing a mixture of two or more polymerizable olefins such as, for example, ethylene/propylene, ethylene/1-butene, ethylene/1-pentene, ethylene/1-hexene, ethylene/4-methyl-1-pentene, ethylene/1-octene, ethylene/styrene, ethylene/propylene/butadiene and other EPDM terpolymers. Preferably, the polyolefin is an ethylene homopolymer, an ethylene/alpha-olefin interpolymer, or an ethylene/alpha-olefin/diene interpolymer (e.g., terpolymer).

The term "copolymer" means a polymer prepared from two or more monomers, which form repeat units of the polymer. The terms "interpolymer" and "copolymer" are used interchangeably herein and do not imply any particular distribution of the repeat units unless noted otherwise herein.

Preferably, the polyolefin comprises a poly(ethylene alpha-olefin) copolymer, and in some embodiments a poly(ethylene alpha-olefin) block copolymer prepared according to an aforementioned preferred process of the first embodiment.

The ethylene/α-olefin multi-block interpolymers described herein can be blended with one or more other polymers to form polymer compositions. The one or more other polymers include substantially linear ethylene interpolymers or homopolymers (SLEP), high pressure low density polyethylene (LDPE), ethylene/vinyl acetate copolymer (EVA), ethylene/carboxylic acid copolymers and ionomers thereof, polybutylene (PB), and α-olefin polymers such as high density polyethylene, medium density polyethylene, polypropylene, ethylene/propylene interpolymers, linear low density polyethylene (LLDPE) and ultra low density polyethylene, as well as graft-modified polymers, and combinations thereof including density, MWD, and/or comonomer combinations such as those disclosed, for example, in U.S. Pat. No. 5,032,463.

Often it is desirable to include in the polymer compositions an additional polymer or polymer blend made with a Ziegler catalyst, a constrained geometry catalyst, or a combination thereof. Particularly useful second polymers include for example, SLEP, LLDPE, LDPE and blends thereof such as described in, for example, U.S. Pat. Nos. 5,844,045; 5,847,053 and 6,111,023. Such polymers are sold commercially under the names AFFINITY®, Elite®, Dowlex®, all of The Dow Chemical Company (Midland, Mich., USA), and Exact® of Exxon Mobil Corporation (Irving, Tex., USA).

The polymer compositions described in the immediately two preceding paragraphs can be formed by any convenient method. For example, the blends may be prepared by mixing or kneading the respective components at a temperature around or above the melt point temperature of one or more of the components. For most ethylene/α-olefin multi-block interpolymer compositions, this temperature may be above 130° C., most generally above 145° C., and most preferably above 150° C. Typical polymer mixing or kneading equipment that is capable of reaching the desired temperatures and melt plastifying the mixture may be employed. These include mills, kneaders, extruders (both single screw and twin-screw), Banbury mixers, calenders, and the like. The sequence of mixing and method may depend on the final composition. A combination of Banbury batch mixers and continuous mixers may also be employed, such as a Banbury mixer followed by a mill mixer followed by an extruder.

Another method of forming the polymer compositions comprises in-situ polymerization as disclosed in U.S. Pat. No. 5,844,045. U.S. Pat. No. 5,844,045 describes inter alia, interpolymerizations of ethylene and ($C_3$-$C_{20}$)alpha-olefins using at least one homogeneous catalyst in at least one reactor and at least one heterogeneous catalyst in at least one other reactor. The multiple reactors can be operated in series or in parallel or any combination thereof, with at least one reactor employed to make an ethylene/α-olefin multi-block interpolymer as described above. In this manner, blends may be made in solution processes comprising constrained geometry catalysts, Ziegler catalysts, and combinations thereof. Such blends comprise, for example, one or more ethylene/α-olefin multi-block interpolymers (as described above and in U.S. Pat. No. 7,622,529 B2 and U.S. patent family members thereof, one or more polymers of broad molecular weight distribution (e.g. heterogeneously branched ethylene polymers as described in, for example, U.S. Pat. No. 5,847,053), and/or one or more polymers of narrow molecular weight distribution (e.g., homogeneous polymers as described in U.S. Pat. No. 3,645,992 or 5,272,236).

In other embodiments the poly(ethylene alpha-olefin) copolymer is the aforementioned poly(ethylene alpha-olefin) block copolymer. The poly(ethylene alpha-olefin) block copolymer comprises an ethylene-derived hard segment (i.e., polyethylene hard segment) and a soft segment comprising residuals from the alpha-olefin and ethylene. The residuals of the alpha-olefin and ethylene typically are approximately randomly distributed in the soft segment. Preferably, the polyethylene hard segment is characterizable as having less than 5 mole percent (mol %) of a residual of the alpha-olefin covalently incorporated therein, as determined by nuclear magnetic resonance as described later.

The poly(ethylene alpha-olefin) block copolymers comprise ethylene residuals and one or more copolymerizable α-olefin comonomer residuals (i.e., ethylene and one or more copolymerizable α-olefin comonomers in polymerized form). The poly(ethylene alpha-olefin) block copolymers are characterized by multiple blocks or segments of two or more polymerized monomer units differing in chemical or physical properties. That is, the ethylene/α-olefin interpolymers are block interpolymers, preferably multi-block interpolymers or copolymers.

In some embodiments, the multi-block copolymer can be represented by the following formula:

where n is at least 1, preferably an integer greater than 1, such as 2, 3, 4, 5, 10, 15, 20, 30, 40, 50, 60, 70, 80, 90, 100, or higher, "A" represents a hard block or segment and "B" represents a soft block or segment. Preferably, As and Bs are linked in a linear fashion, not in a branched or a star fashion.

"Hard" segments refer to blocks of polymerized units in which ethylene residuals are present in an amount greater than 95 weight percent, and preferably greater than 98 weight percent in the poly(ethylene alpha-olefin) block copolymers. In other words, the comonomer (i.e., alpha-olefin) residuals content in the hard segments is less than 5 weight percent, and preferably less than 2 weight percent. In some embodiments, the hard segments comprise all or substantially all ethylene residuals. The phrases "polyethylene hard segment" and "ethylene-derived hard segment" are synonymous and mean the hard segment portion of a poly(ethylene alpha-olefin) block copolymer.

"Soft" segments refer to blocks of polymerized units in which the comonomer (i.e., alpha-olefin) residuals content is greater than 5 weight percent, preferably greater than 8 weight percent, greater than 10 weight percent, or greater than 15 weight percent in the poly(ethylene alpha-olefin) block copolymers. In some embodiments, the comonomer residuals content in the soft segments can be greater than 20 weight percent, greater than 25 eight percent, greater than 30 weight percent, greater than 35 weight percent, greater than 40 weight percent, greater than 45 weight percent, greater than 50 weight percent, or greater than 60 weight percent.

In some embodiments, A blocks and B blocks are randomly distributed along a polymer (backbone) chain of the poly (ethylene alpha-olefin) block copolymer. In other words, the poly(ethylene alpha-olefin) block copolymers usually do not have a structure like:

AAA-AA-BBB-BB.

In other embodiments, the poly(ethylene alpha-olefin) block copolymers usually do not have a third type of block, i.e., do not have a "C" block that is not an A block and not a B block. In still other embodiments, each of block A and block B of the poly(ethylene alpha-olefin) block copolymers has monomers or comonomers randomly distributed within the block. In other words, neither block A nor block B comprises two or more segments (or sub-blocks) of distinct composition, such as a tip segment, which has a different composition than the rest of the block.

In some embodiments, the polyolefin comprises an ethylene/α-olefin interpolymer, such as those described in U.S. Provisional Patent Application No. 61/024,674 and family member PCT International Patent Application Publication Number WO 2009/097560, which are herein incorporated by reference, preferably a block copolymer, which comprises a hard segment and a soft segment, and is characterized by a $M_w/M_n$ in the range of from about 1.4 to about 2.8 and:

(a) has at least one $T_m$ (° C.), and a density (d) in grams/cubic centimeter, wherein the numerical values of $T_m$ and d correspond to the relationship:

$$T_m > -6553.3 + 13735(d) - 7051.7(d)^2, \text{ or}$$

(b) is characterized by a heat of fusion (ΔH, in J/g), and a delta temperature quantity (ΔT, in ° C.), defined as the temperature difference between the tallest differential scanning calorimetry (DSC) peak and the tallest crystallization analysis fractionation (CRYSTAF) peak, wherein the numerical values of ΔT and ΔH have the following relationships:

$$\Delta T > -0.1299(\Delta H) + 62.81 \text{ for } \Delta H \text{ greater than zero (0) and up to } 130 \text{ J/g,}$$

$$\Delta T \geq 48° \text{ C. for } \Delta H \text{ greater than } 130 \text{ J/g,}$$

wherein the CRYSTAF peak is determined using at least 5 percent of the cumulative polymer, and if less than 5 percent of the polymer has an identifiable CRYSTAF peak, then the CRYSTAF temperature is 30° C.; or (c) is characterized by an elastic recovery ($R_e$) in percent at 300 percent strain and 1 cycle measured with a compression-molded film of the ethylene/α-olefin interpolymer, and has a density (d) in grams/cubic centimeter, wherein the numerical values of $R_e$ and d satisfy the following relationship when ethylene/α-olefin interpolymer is substantially free of a cross-linked phase:

$$R_e > 1481 - 1629(d); \text{ or}$$

(d) has a molecular fraction which elutes between 40° C. and 130° C. when fractionated using TREF, characterized in that the fraction has a molar comonomer content of at least 5 percent higher than that of a comparable random ethylene interpolymer fraction eluting between the same temperatures, wherein said comparable random ethylene interpolymer has the same comonomer(s) and has a melt index, density, and molar comonomer content (based on the whole polymer) within 10 percent of that of the ethylene/α-olefin interpolymer; or (e) has a storage modulus at 25° C. (G'(25° C.)) and a storage modulus at 100° C. (G'(100° C.)) wherein the ratio of G'(25° C.) to G'(100° C.) is in the range of about 1:1 to about 9:1; or (f) is characterized by an average block index greater than zero (0) and up to about 1.0; or (g) has a molecular fraction which elutes between 40° C. and 130° C. when fractionated using TREF, characterized in that the fraction has a molar comonomer content greater than, or equal to, the quantity (−0.2013)T+20.07, more preferably greater than or equal to the quantity (−0.2013)T+21.07, where T is the numerical value of the peak elution temperature of the TREF fraction, measured in ° C.; and, wherein the ethylene/α-olefin block interpolymer is mesophase separated.

In some embodiments, the polyolefin comprises an ethylene/α-olefin interpolymer, such as that described in U.S. Pat. No. 7,355,089 and U.S. Patent Application Publication No. US 2006-0199930, wherein the interpolymer is preferably a block copolymer, and comprises a hard segment and a soft segment, and the ethylene/α-olefin interpolymer:

(a) has a $M_w/M_n$ from about 1.7 to about 3.5, at least one $T_m$ (° C.), and a density d, in grams/cubic centimeter, wherein the numerical values of $T_m$ and d correspond to the relationship:

$$Tm > -2002.9 + 4538.5(d) - 2422.2(d)2; \text{ or}$$

(b) has a $M_w/M_n$ from about 1.7 to about 3.5, and is characterized by a heat of fusion, ΔH in J/g, and a delta quantity, ΔT (° C.), defined as the temperature difference between the tallest DSC peak and the tallest CRYSTAF peak, wherein the numerical values of ΔT and ΔH have the following relationships:

$$\Delta T > -0.1299(\Delta H) + 62.81 \text{ for } \Delta H \text{ greater than zero and up to } 130 \text{ J/g,}$$

$$\Delta T \geq 48° \text{ C. for } \Delta H \text{ greater than } 130 \text{ J/g,}$$

wherein the CRYSTAF peak is determined using at least 5 percent of the cumulative polymer, and if less than 5 percent of the polymer has an identifiable CRYSTAF peak, then the CRYSTAF temperature is 30° C.; or (c) is characterized by an $R_e$ in percent at 300 percent strain and 1 cycle measured with a compression-molded film of the ethylene/α-olefin interpolymer, and has a density, d, in grams/cubic centimeter, wherein the numerical values of $R_e$ and d satisfy the following relationship when ethylene/α-olefin interpolymer is substantially free of a cross-linked phase:

$$R_e > 1481 - 1629(d); \text{ or}$$

(d) has a molecular fraction which elutes between 40° C. and 130° C. when fractionated using TREF, characterized in that the fraction has a molar comonomer content of at least 5 percent higher than that of a comparable random ethylene interpolymer fraction eluting between the same temperatures, wherein said comparable random ethylene interpolymer has the same comonomer(s) and has a melt index, density, and molar comonomer content (based on the whole polymer) within 10 percent of that of the ethylene/α-olefin interpolymer; or (e) has a storage modulus at 25° C. (G'(25° C.)), and a storage modulus at 100° C., (G'(100° C.)), wherein the ratio of G'(25° C.) to G'(100° C.) is in the range of about 1:1 to about 9:1 or (f) has a molecular fraction which elutes between 40° C. and 130° C. when fractionated using TREF, characterized in that the fraction has a block index of at least 0.5 and up to about 1 and a $M_w/M_n$ greater than about 1.3; or (g) has an average block index greater than zero (0) and up to about 1.0 and a $M_w/M_n$ greater than about 1.3; or (h) has a molecular fraction which elutes between 40° C. and 130° C. when fractionated using TREF, characterized in that the fraction has a molar comonomer content greater than, or equal to, the quantity (−0.2013)T+20.07, more preferably greater than or equal to the quantity (−0.2013) T+21.07, where T is the numerical value of the peak elution temperature of the TREF fraction, measured in ° C.

Other embodiments comprise polymers and processes such as those described in PCT International Patent Application Publication Nos. WO 2005/090425, WO 2005/090426, and WO 2005/090427.

Monomer and any comonomer content of the polyolefins may be measured using any suitable technique such as, for example, infrared (IR) spectroscopy and nuclear magnetic resonance (NMR) spectroscopy, with techniques based on NMR spectroscopy being preferred and carbon-13 NMR spectroscopy being more preferred. The NMR spectroscopy methods are as described later in the Materials and Methods.

In some embodiments, the amount of olefin comonomer incorporated into the poly(olefin monomer-olefin comonomer) block copolymer or segments thereof is characterized by a comonomer incorporation index. As used herein, the term, "comonomer incorporation index", refers to the mole percent of residuals of olefin comonomer incorporated into olefin monomer/comonomer copolymer, or segment thereof, prepared under representative olefin polymerization conditions. Preferably, the olefin monomer is ethylene or propylene and the comonomer respectively is an $(C_3-C_{40})$alpha-olefin or $(C_4-C_{40})$alpha-olefin. The olefin polymerization conditions are ideally under steady-state, continuous solution polymerization conditions in a hydrocarbon diluent at 100° C., 4.5 megapascals (MPa) ethylene (or propylene) pressure (reactor pressure), greater than 92 percent (more preferably greater than 95 percent) olefin monomer conversion, and greater than 0.01 percent olefin comonomer conversion. The selection of catalyst compositions, which include the invention catalyst, having the greatest difference in olefin comonomer incorporation indices results in poly(olefin monomer-olefin comonomer) block copolymers from two or more olefin monomers having the largest difference in block or segment properties, such as density.

In certain circumstances the comonomer incorporation index may be determined directly, for example by the use of NMR spectroscopic techniques described previously or by IR spectroscopy. If NMR or IR spectroscopic techniques cannot be used, then any difference in comonomer incorporation is indirectly determined. For polymers formed from multiple monomers this indirect determination may be accomplished by various techniques based on monomer reactivities.

For copolymers produced by a given catalyst, the relative amounts of comonomer and monomer in the copolymer and hence the copolymer composition are determined by relative rates of reaction of comonomer and monomer. Mathematically the molar ratio of comonomer to monomer is given by the equations described in US 2007/0167578 A1, in paragraphs numbered [0081] to [0090].

For this model as well the polymer composition is a function only of temperature dependent reactivity ratios and comonomer mole fraction in the reactor. The same is also true when reverse comonomer or monomer insertion may occur or in the case of the interpolymerization of more than two monomers.

Reactivity ratios for use in the foregoing models may be empirically derived from actual polymerization data. Suitable theoretical techniques are disclosed, for example, in B. G. Kyle, *Chemical and Process Thermodynamics*, Third Edition, Prentice-Hall, 1999 and in Redlich-Kwong-Soave (RKS) Equation of State, *Chemical Engineering Science*, 1972, pp 1197-1203. Commercially available software programs may be used to assist in deriving reactivity ratios from experimentally derived data. One example of such software is Aspen Plus from Aspen Technology, Inc., Ten Canal Park, Cambridge, Mass. 02141-2201 USA.

At times it is convenient to incorporate by reference examples of an associate olefin polymerization catalyst that can be used in embodiments of the invention process for polymerizing an olefin comprising chain shuttling and employing the invention catalyst. For convenience and consistency, one of the invention catalyst and associate olefin polymerization catalyst are thus sometimes referred to herein using generic terms such as a "first olefin polymerization catalyst" and one as a "second olefin polymerization catalyst" or vice versa. That is, in some embodiments, the first olefin polymerization catalyst is the same as the invention catalyst and the second olefin polymerization catalyst is the same as the associate olefin polymerization catalyst; and vice versa in other embodiments. In some embodiments, the first and second olefin polymerization catalysts each independently is an invention catalyst. As used herein, the first olefin polymerization catalyst is characterizable as having a high comonomer incorporation index and the second olefin polymerization catalyst is characterizable as having a comonomer incorporation index that is less than 95 percent of the high comonomer incorporation index. Preferably, the second olefin polymerization catalyst is characterized as having a comonomer incorporation index that is less than 90 percent, more preferably less than 50 percent, still more preferably less than 25 percent, and even more preferably less than 10 percent of the high comonomer incorporation index of the first olefin polymerization catalyst.

When preparing the poly(ethylene alpha-olefin) block copolymer according to the preferred process of the first embodiment, the invention catalyst is employed as part of a catalyst system, the catalyst system comprising a mixture or reaction product of:

(A) a first olefin polymerization catalyst, the first olefin polymerization catalyst being characterized as having a high comonomer incorporation index;

(B) a second olefin polymerization catalyst, the second olefin polymerization catalyst being characterized as having a comonomer incorporation index that is less than 90 percent of the comonomer incorporation index of the first olefin polymerization catalyst; and (C) a chain shuttling agent;

the invention catalyst being either the first or second olefin polymerization catalyst.

The term "catalyst" as generally used herein may refer to an unactivated form of a metal-ligand complex (i.e., precursor) or, preferably, the activated form thereof (e.g., after contact of the unactivated form with an activating cocatalyst to give a catalytically active mixture or product thereof). For the associate olefin polymerization catalyst comprising or prepared from a non-invention metal-ligand complex, a metal of the non-invention metal-ligand complex can be a metal of any one of Groups 3 to 15, preferably Group 4, of the Periodic Table of the Elements. Examples of types of suitable non-invention metal-ligand complexes are metallocene, half-metallocene, constrained geometry, and polyvalent pyridylamine-, polyether-, or other polychelating base complexes. Such non-invention metal-ligand complexes are described in the WO 2008/027283 and corresponding U.S. patent application Ser. No. 12/377,034. Other suitable non-invention metal-ligand complexes are those described in U.S. Pat. Nos. 5,064,802; 5,153,157; 5,296,433; 5,321,106; 5,350,723; 5,425,872; 5,470,993; 5,625,087; 5,721,185; 5,783,512; 5,866,704; 5,883,204; 5,919,983; 6,015,868; 6,034,022; 6,103,657; 6,150,297; 6,268,444; 6,320,005; 6,515,155; 6,555,634; 6,696,379; 7,163,907; and 7,355,089, as well as in applications WO 02/02577; WO 02/92610; WO 02/38628; WO 03/40195; WO 03/78480; WO 03/78483; WO 2009/012215 A2; US 2003/0004286; and US 04/0220050; US 2006/0199930 A1; US 2007/0167578 A1; and US 2008/0311812 A1.

The "first olefin polymerization catalyst" is interchangeably referred to herein as "Catalyst (A)." The "second olefin polymerization catalyst" is interchangeably referred to herein as "Catalyst (B)." The selection of metal complexes or catalyst compositions having the greatest difference in comonomer incorporation indices results in copolymers from two or more monomers having the largest difference in block or segment properties, such as density.

Preferably, the comonomer incorporation index of Catalyst (B) is less than 50 percent and more preferably less than 5 percent of the comonomer incorporation index of Catalyst (A). An example of Catalyst (B) is the aforementioned "associate olefin catalyst."

In some embodiments, the invention catalyst is Catalyst (A), but not Catalyst (B). In such embodiments, preferably the Catalyst (B) of the catalyst system is a Catalyst (B) described in US 2006/0199930 A1; US 2007/0167578 A1; US 2008/0311812 A1; U.S. Pat. No. 7,355,089 B2; or WO 2009/012215 A2.

In some embodiments, the invention catalyst is Catalyst (B), but not Catalyst (A). In such embodiments, preferably the Catalyst (A) of the catalyst system is a Catalyst (A) described in US 2006/0199930 A1; US 2007/0167578 A1; US 2008/0311812 A1; U.S. Pat. No. 7,355,089 B2; or WO 2009/012215 A2.

Representative Catalysts (A) and (B) of US 2006/0199930 A1; US 2007/0167578 A1; US 2008/0311812 A1; U.S. Pat. No. 7,355,089 B2; or WO 2009/012215 A2 are the catalysts of formulas (A1) to (A5), (B1), (B2), (C1) to (C3), and (D1):

Catalyst (A1) is [N-(2,6-di(1-methylethyl)phenyl)amido) (2-isopropylphenyl)(α-naphthalen-2-diyl(6-pyridin-2-diyl) methane)]hafnium dimethyl, prepared according to the teachings of WO 03/40195, 2003US0204017, U.S. Ser. No. 10/429,024, filed May 2, 2003, and WO 04/24740, and having the structure:

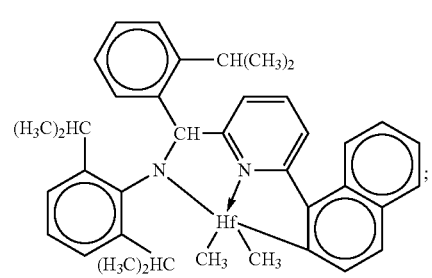

Catalyst (A2) is [N-(2,6-di(1-methylethyl)phenyl)amido) (2-methylphenyl)(1,2-phenylene-(6-pyridin-2-diyl)methane)]hafnium dimethyl, prepared according to the teachings of WO 03/40195, 2003US0204017, U.S. Ser. No. 10/429, 024, filed May 2, 2003, and WO 04/24740, and having the structure:

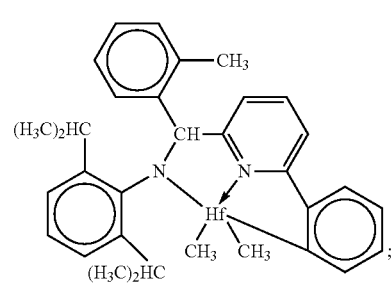

Catalyst (A3) is bis[N,N'''-(2,4,6-tri(methylphenyl)amido) ethylenediamine]hafnium dibenzyl, and having the structure:

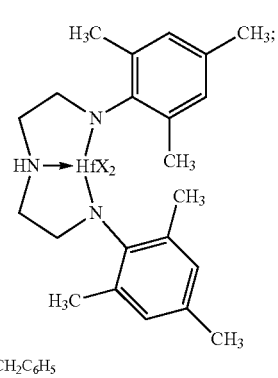

Catalyst (A4) is bis((2-oxoyl-3-(dibenzo-1H-pyrrole-1-yl)-5-(methyl)phenyl)-2-phenoxymethyl)cyclohexane-1,2-diyl zirconium(IV)dibenzyl, prepared substantially according to the teachings of US-A-2004/0010103, and having the structure:

(A4)

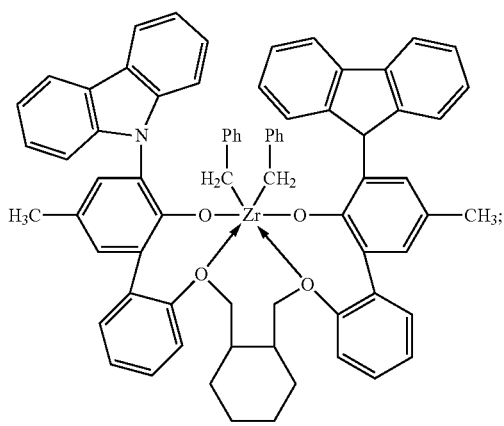

Catalyst (A5) is [η²-2,6-diisopropyl-N-(2-methyl-3-(octylimino)butan-2-yl)benzeneamide]trimethylhafnium, prepared substantially according to the teachings of WO 2003/051935, and having the structure:

(A5)

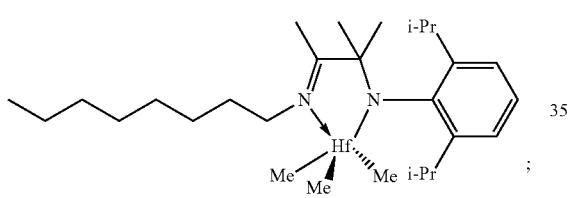

Catalyst (B1) is 1,2-bis-(3,5-di-t-butylphenylene)(1-(N-(1-methylethyl)imino)methyl)(2-oxoyl)zirconium dibenzyl, and having the structure:

(B1)

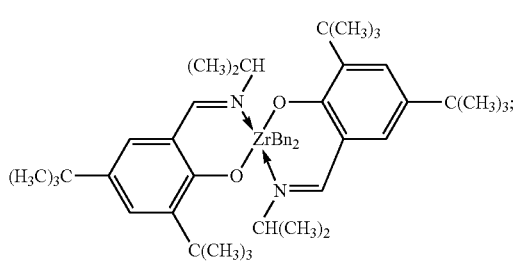

Bn = CH₂C₆H₅

Catalyst (B2) is 1,2-bis-(3,5-di-t-butylphenylene)(1-(N-(2-methylcyclohexyl)-imino)methyl)(2-oxoyl) zirconium dibenzyl, and having the structure:

(B2)

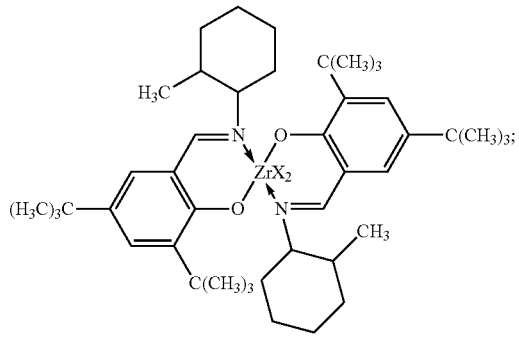

X = CH₂C₆H₅

Catalyst (C1) is (t-butylamido)dimethyl(3-N-pyrrolyl-1,2,3,3a,7a-η-inden-1-yl)silanetitanium dimethyl, prepared substantially according to the techniques of U.S. Pat. No. 6,268,444, and having the structure:

(C1)

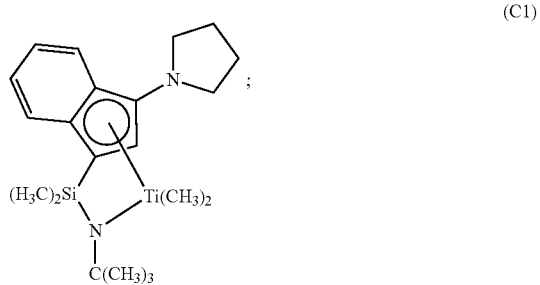

Catalyst (C2) is (t-butylamido)di(4-methylphenyl)(2-methyl-1,2,3,3a,7a-η-inden-1-yl)silanetitanium dimethyl, prepared substantially according to the teachings of US-A-2003/004286, and having the structure:

(C2)

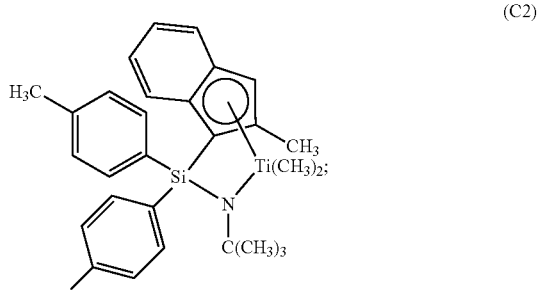

Catalyst (C3) is (t-butylamido)di(4-methylphenyl)(2-methyl-1,2,3,3a,8a-η-s-indacen-1-yl)silanetitanium dimethyl, prepared substantially according to the teachings of US-A-2003/004286, and having the structure:

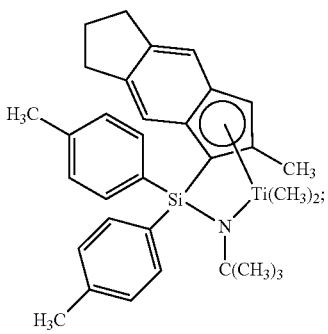

(C3)

and

Catalyst (D1) is bis(dimethyldisiloxane)(indene-1-yl)zirconium dichloride, available from Sigma-Aldrich, and having the structure:

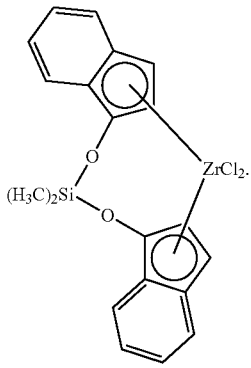

(D1)

As mentioned previously, some embodiments of the invention process for polymerizing an olefin further employ a chain shuttling agent. The terms "chain shuttling agent" and "CSA" are interchangeably used herein and refer to a compound that is characterizable as being capable of causing, under the olefin polymerization conditions, exchange of a polymeryl chain (i.e., polymer chain or fragment) between at least two active catalyst sites of two olefin polymerization catalysts, the two olefin polymerization catalysts being the invention catalyst and the associate olefin polymerization catalyst such as another invention catalyst or one of the non-invention catalysts described previously. That is, transfer of a polymer fragment occurs both to and from one or more of active sites of the olefin polymerization catalysts.

In contrast to a chain shuttling agent, a "chain transfer agent" causes termination of polymer chain growth and amounts to a one-time transfer of polymer from a catalyst (e.g., the invention catalyst) to the transfer agent. In some polymerization process embodiments such as those useful for preparing polyolefin homopolymers and random polyolefin copolymers, the CSA is characterizable of functioning as a chain transfer agent. That is, the CSA is characterizable as functioning in such a way that there is a one-time transfer of a polyolefin homopolymer or random polyolefin copolymer product formed in such polymerization process from the olefin polymerization catalyst (e.g., the invention catalyst) to the CSA. In such embodiments, it is not necessary for the CSA to reversibly chain shuttle, as such embodiments typically employ only one olefin polymerization catalyst, which may have or use only one active catalyst site.

In some embodiments, the chain shuttling agent is characterizable as having a chain shuttling activity ratio $R_{A-B}/R_{B-A}$. In general, for any two catalysts (A) and (B), the chain shuttling activity ratio $R_{A-B}/R_{B-A}$ is calculated by dividing a rate of chain transfer from an active site of a Catalyst (A) to an active site of a Catalyst (B) ($R_{A-B}$) by a rate of chain transfer from the active site of the Catalyst (B) to the active site of the Catalyst (A) ($R_{B-A}$). Preferably the Catalyst (A) is the invention catalyst and the Catalyst (B) is the aforementioned associate olefin polymerization catalyst. For the chain shuttling agent, preferably the chain shuttling activity ratio $R_{A-B}/R_{B-A}$ is from 0.01 to 100. Preferably, an intermediate formed between the chain shuttling agent and the polymeryl chain is sufficiently stable that chain termination is relatively rare. A (polyolefin-polyradical)-containing chain shuttling agent is an example of said intermediates.

By selecting different combinations of olefin polymerization catalysts having differing comonomer incorporation rates (as described herein) as well as differing reactivities, and by combining two or more CSAs (and preferably 3 or less CSAs), different poly(olefin monomer-olefin comonomer) multiblock copolymer products can be prepared in some embodiments of the invention process for polymerizing an olefin. Such different products can have segments of different densities or comonomer concentrations, different block lengths, different numbers of such segments or blocks, or a combination thereof. For example, if the chain shuttling activity of the chain shuttling agent is low relative to a polymer chain propagation rate of one or more of the olefin polymerization catalysts, longer block length multiblock copolymers and polymer blends may be obtained as products. Contrariwise, if chain shuttling is very fast relative to polymer chain propagation, a copolymer product having a more random chain structure and shorter block lengths is obtained. In generally, an extremely fast chain shuttling agent may produce a multiblock copolymer having substantially random copolymer properties. By proper selection of both catalyst(s) and the CSA, relatively pure block copolymers, copolymers containing relatively large polymer segments or blocks, and/or blends of the foregoing with various ethylene or propylene homopolymers and/or copolymers can be obtained as products.

In some embodiments of the invention process for polymerizing an olefin employing the CSAs, the chain shuttling agents that are suitable for use therein include Group 1, 2, 12 or 13 metal compounds or complexes containing at least one ($C_1$-$C_{20}$)hydrocarbyl group, preferably ($C_1$-$C_{12}$)hydrocarbyl substituted aluminum, gallium or zinc compounds, and reaction products thereof with a proton source. Preferred ($C_1$-$C_{20}$) hydrocarbyl groups are alkyl groups, preferably linear or branched, ($C_1$-$C_8$)alkyl groups. Most preferred shuttling agents for use in the present invention are trialkyl aluminum and dialkyl zinc compounds, especially triethylaluminum, tri(i-propyl)aluminum, tri(i-butyl)aluminum, tri(n-hexyl)aluminum, tri(n-octyl)aluminum, triethylgallium, or diethylzinc. Additional suitable shuttling agents include the reaction product or mixture formed by combining the foregoing organometal compound, preferably a tri(($C_1$-$C_8$)alkyl)aluminum or di(($C_1$-$C_8$)alkyl)zinc compound, especially triethylaluminum, tri(i-propyl)aluminum, tri(i-butyl)aluminum, tri(n-hexyl)aluminum, tri(n-octyl)aluminum, or diethylzinc, with less than a stoichiometric quantity (relative to the number of hydrocarbyl groups) of a primary or secondary amine, primary or secondary phosphine, thiol, or hydroxyl compound, especially bis(trimethylsilyl)amine, t-butyl(dimethyl)silanol, 2-hydroxymethylpyridine, di(n-pentyl)amine, 2,6-di(t-butyl) phenol, ethyl(1-naphthyl)amine, bis(2,3,6,7-dibenzo-1-azacycloheptaneamine), diphenylphosphine, 2,6-di(t-butyl) thiophenol, or 2,6-diphenylphenol. Desirably, sufficient amine, phosphine, thiol, or hydroxyl reagent is used such that at least one hydrocarbyl group remains per metal atom. The primary reaction products of the foregoing combinations most desired for use in the present invention as shuttling agents are n-octylaluminum di(bis(trimethylsilyl)amide), i-propylaluminum bis(dimethyl(t-butyl)siloxide), and n-octylaluminum di(pyridinyl-2-methoxide), i-butylaluminum bis(dimethyl(t-butyl)siloxane), i-butylaluminum di(bis(trimethylsilyl)amide), n-octylaluminum di(pyridine-2-methoxide), i-butylaluminum bis(di(n-pentyl)amide), n-octylaluminum bis(2,6-di-t-butylphenoxide), n-octylaluminum di(ethyl (1-naphthyl)amide), ethylaluminum bis(t-butyldimethylsiloxide), ethylaluminum di(bis (trimethylsilyl)amide), ethylaluminum bis(2,3,6,7-dibenzo-1-azacycloheptaneamide), n-octylaluminum bis(2,3,6,7-dibenzo-1-azacycloheptaneamide), n-octylaluminum bis (dimethyl(t-butyl)siloxide, ethylzinc(2,6-diphenylphenoxide), and ethylzinc(t-butoxide). Other suitable non-invention chain shuttling agents are described in WO 2005/073283 A1; WO 2005/090425 A1; WO 2005/090426A1; WO 2005/090427 A2; WO 2006/101595 A1; WO 2007/035485 A1; WO 2007/035492 A1; and WO 2007/035493 A2.

Preferably, the invention processes employ three or fewer, more preferably two, and still more preferably one metal-ligand complex of formula (I). Also preferably, the invention processes employ the one or more metal-ligand complexes of formula (I) (ingredient (a)) and the one or more activating co-catalysts (ingredient (b)) that comprise or derive a catalyst, wherein the catalyst is characterized as having a catalyst efficiency of greater than 110,000, more preferably greater than 130,000, and still more preferably greater than 210,000, wherein the catalyst efficiency is calculated by dividing the number of grams of polyolefin prepared by the number of grams of metal (M) of ingredient (a) (i.e., metal complex of formula (I)) employed at a reaction mixture temperature of 120° C. or 135° C. using respective conditions as described later in the Examples, especially conditions of Example F1 for 120° C. and conditions of Example E of 135° C.

Turning to the metal-ligand complex of formula (I), in some embodiments M is a metal of Group 3. Group 3 metals (symbol), including lanthanoids and actinoids, useful in the present invention are scandium (Sc), yttrium (Y), the lanthanides (sometimes called lanthanoids), especially lanthanum (La), cerium (Ce), praseodymium (Pr), neodymium (Nd), promethium (Pm), samarium (Sm), europium (Eu), gadolinium (Gd), terbium (Tb), dysprosium (Dy), holium (Ho), erbium (Er), thulium (Tm), ytterbium (Yb), and lutetium (Lu), and the stable actinides (sometimes called actinoids), especially stable isotopes of actinium (Ac), thorium (Th), and uranium (U). Unstable actinides such as protactinium (Pa), neptunium (Np), plutonium (Pu), americium (Am), curium (Cm), berkelium (Bk), californium (Cf), einsteinium (Es) fermium (Fm), mendelevium (Md), nobelium (No), and lawrencium (Lr) are excluded from the actinides useful in the present invention. Preferred Group 3 metals are Sc and Y. In other embodiments M is a metal of Group 4. Preferred Group 4 metals are those in a formal oxidation state of +2, +3, or +4, more preferably +4. For purposes of the present invention, rutherfordium (Rf) is excluded from the Group 4 metals useful in the present invention. In still other embodiments M is a metal of Group 5. Group 5 metals useful in the present invention are vanadium (V), niobium (Nb), and tantalum (Ta). For purposes of the present invention, dubnium (Db) is excluded from the Group 5 metals useful in the present invention. In still other embodiments M is a metal of Group 6. Group 6 metals useful in the present invention are chromium (Cr), molybdenum (Mo), and tungsten (W). For purposes of the present invention, seaborgium (Sg) is excluded from the Group 6 metals useful in the present invention.

More preferably, M is a metal of Group 4, which means that M is titanium (Ti), zirconium (Zr), or hafnium (Hf), and more preferably zirconium or hafnium. In some embodiments M is zirconium. In some embodiments M is hafnium.

In some embodiments n is 1. In some embodiments n is 2. In some embodiments n is 3. In some embodiments n is 4. In some embodiments n is 5.

In some embodiments each X is the monodentate ligand. In some embodiments the monodentate ligand is the monoanionic ligand. The monoanionic ligand has a net formal oxidation state of −1. Each monoanionic ligand preferably independently is hydride, $(C_1-C_{40})$hydrocarbyl carbanion, $(C_1-C_{40})$heterohydrocarbyl carbanion, halide, nitrate, carbonate, phosphate, sulfate, $HC(O)O^-$, $(C_1-C_{40})$hydrocarbyl$C(O)O^-$, $HC(O)N(H)^-$, $(C_1-C_{40})$hydrocarbyl$C(O)N(H)^-$, $(C_1-C_{40})$hydrocarbyl$C(O)N((C_1-C_{20})$hydrocarbyl$)^-$, $R^K R^L B^-$, $R^K R^L N^-$, $R^K O^-$, $R^K S^-$, $R^K R^L P^-$, or $R^M R^K R^L Si^-$, wherein each $R^K$, $R^L$, and $R^M$ independently is hydrogen, $(C_1-C_{40})$hydrocarbyl, or $(C_1-C_{40})$heterohydrocarbyl, or $R^K$ and $R^L$ are taken together to form a $(C_2-C_{40})$hydrocarbylene or $(C_1-C_{40})$heterohydrocarbylene and $R^M$ is as defined above.

In some embodiments the monodentate ligand is the neutral ligand. Preferably the neutral ligand is a neutral Lewis base group that is $R^X NR^K R^L$, $R^K OR^L$, $R^K SR^L$, or $R^X PR^K R^L$, wherein each $R^X$ independently is hydrogen, $(C_1-C_{40})$hydrocarbyl, $[(C_1-C_{10})$hydrocarbyl$]_3 Si$, $[(C_1-C_{10})$hydrocarbyl$]_3 Si$ $(C_1-C_{10})$hydrocarbyl, or $(C_1-C_{40})$heterohydrocarbyl and each $R^K$ and $R^L$ independently is as defined above.

In some embodiments, each monodentate X is a halogen atom, unsubstituted $(C_1-C_{20})$hydrocarbyl, unsubstituted $(C_1-C_{20})$hydrocarbyl$C(O)O—$, or $R^K R^L N—$ wherein each of $R^K$ and $R^L$ independently is an unsubstituted $(C_1-C_{20})$hydrocarbyl. In some embodiments each monodentate X is a chlorine atom, $(C_1-C_{10})$hydrocarbyl (e.g., $(C_1-C_6)$alkyl or benzyl), unsubstituted $(C_1-C_{10})$hydrocarbyl$C(O)O—$, or $R^K R^L N—$ wherein each of $R^K$ and $R^L$ independently is an unsubstituted $(C_1-C_{10})$hydrocarbyl.

In some embodiments two X are taken together to form the bidentate ligand. In some embodiments the bidentate ligand is a neutral bidentate ligand. Preferably the neutral bidentate ligand is a diene of formula $(R^D)_2 C=C(R^D)—C(R^D)=C(R^D)_2$, wherein each $R^D$ independently is H, unsubstituted $(C_1-C_6)$alkyl, phenyl, or naphthyl. In some embodiments the bidentate ligand is a monoanionic-mono(Lewis base) ligand. The monoanionic-mono(Lewis base) ligand preferably is a 1,3-dionate of formula (D): $R^E—C(O^-)=CH—C(=O)—R^E$ (D), wherein each $R^D$ independently is H, unsubstituted $(C_1-C_6)$alkyl, phenyl, or naphthyl. In some embodiments the bidentate ligand is a dianionic ligand. The dianionic ligand has a net formal oxidation state of −2. Preferably each dianionic ligand independently is carbonate, oxalate (i.e., $^-O_2 CC(O)O^-$), $(C_2-C_{40})$hydrocarbylene dicarbanion, $(C_1-C_{40})$heterohydrocarbylene dicarbanion, phosphate, or sulfate. Number and charge (neutral, monoanionic, dianionic) of X are selected depending on the formal oxidation state of M such that the metal-ligand complex of formula (I) is, in aggregate, neutral.

Preferably n is 2 or 3 and at least two X independently are monoanionic monodentate ligands and a third X, if present, is a neutral monodentate ligand.

As used herein, the term "carbonate" means an ionic substance consisting of zero or one cations $Q^X$ and an anion of the empirical formula $CO_3^{-2}$, the ionic substance having an overall −1 or −2 charge. The term "nitrate" means an ionic substance consisting of an anion of the empirical formula $NO_3^-$, the ionic substance having an overall −1 charge. The term "oxalate" means an ionic substance consisting of zero or one cations $Q^X$ and an anion of the empirical formula $^-OC(O)C(O)O^-$, the ionic substance having an overall −1 or −2 charge. The term "phosphate" means an ionic substance consisting of zero, one, or two cations $Q^X$ and an anion of the empirical formula $PO_4^{-3}$, the ionic substance having an overall −1, −2, or −3 charge. The term "sulfate" means an ionic substance consisting of zero or one cations $Q^X$ and an anion of the empirical formula $SO_4^{-2}$, the ionic substance having an overall −1 or −2 charge. In each of the ionic substances, preferably $Q^X$ independently is an inorganic cation of hydrogen atom, lithium, sodium, potassium, calcium, or magnesium, including hemi calcium and hemi magnesium.

In some embodiments each of $R^1$ to $R^6$ is a hydrogen atom. In some embodiments at least one but not all of $R^1$ to $R^6$ is a hydrogen atom and each of the remainder, and more preferably at least two of $R^1$ to $R^6$ independently is $(C_1-C_{40})$hydrocarbyl, $(C_1-C_{40})$heterohydrocarbyl, $(C_1-C_{40})$hydrocarbyl-O—, or halogen atom. Preferably at least $R^1$ is $(C_1-C_{40})$hydrocarbyl, $(C_1-C_{40})$heterohydrocarbyl, $(C_1-C_{40})$hydrocarbyl-O—, or halogen atom, and more preferably $(C_1-C_{40})$hydrocarbyl.

In some embodiments $R^7$ is a $(C_1-C_{40})$hydrocarbyl, preferably a $(C_6-C_{40})$hydrocarbyl, and more preferably a $(C_6-C_{40})$aryl. Preferably the $(C_6-C_{40})$aryl is a phenyl, more preferably a phenyl having at least one substituent in an ortho-position (i.e., 2- or 6-position), and still more preferably a phenyl independently having a substituent in each ortho-position (i.e., 2- and 6-position).

In some embodiments $R^7$ is a $(C_1-C_{40})$heterohydrocarbyl, and preferably a $(C_1-C_{40})$heteroaryl. In some embodiments $R^7$ is not quinolin-8-yl.

In any one of the metal-ligand complexes of the aforementioned formulas having $R^7$, especially preferred is such a metal-ligand complex wherein $R^7$ is 2,6-bis(di($C_1-C_4$)alkyl-amino)phenyl; 2,6-dinitrophenyl; 2,6-di(($C_1-C_4$)alkyloxy)phenyl; 2-($C_1-C_4$)alkyl-phenyl; isopropylphenyl; 2,6-di($C_1-C_4$)alkyl-phenyl; 2,6-dimethylphenyl; 2,6-diisopropylphenyl; 3,5-di($C_1-C_4$)alkyl-phenyl; 2,4,6-tri($C_1-C_4$)alkyl-phenyl; biphenyl-2-yl; 2,6-diphenylphenyl; diphenylphenyl; 2,4,6-triphenylphenyl; 3,5-bis(2,6-bis[$C_1-C_4$)alkyl]phenyl)phenyl; 2,6-di(1-naphthyl)phenyl; 3,5-di(1-naphthyl)phenyl; cyclohexyl; diphenylmethyl; or trityl; wherein each $(C_1-C_4)$alkyl independently is methyl, ethyl, 1-propyl, 1-methylethyl, 1-butyl, 2-butyl, 2-methylpropyl, or 1,1-dimethylethyl. Also especially preferred is the metal-ligand complex wherein $R^7$ is $(C_1-C_{20})$alkyl (e.g., 1-butyl, 2-propyl, 1,1-dimethylethyl, and 1-octyl), benzyl, phenyl, cyclohexyl, 1-methyl-piperidin-4-yl, 3-(N,N-di(($C_1-C_4$)alkyl)amino)-propyl, $(C_1-C_4)$alkyl-amino, or pyrrol-1-yl.

In some embodiments, at least one, more preferably at least two, still more preferably all of $R^1$ to $R^7$ and X independently are unsubstituted (i.e., lack substituents $R^S$). In other embodiments, at least one, more preferably two, and still more preferably 3 of $R^1$ to $R^7$ and X are independently substituted with the substituent $R^S$, each substituent $R^S$ independently and preferably being a $(C_1-C_{10})$alkyl, and more preferably a $(C_1-C_5)$alkyl. In other embodiments, the metal-ligand complex of formula (I) is as described in the first embodiment, except wherein one radical group (e.g., $(C_1-C_{40})$hydrocarbyl or $(C_1-C_{40})$hydrocarbylC(O)O$^-$) is deleted from the definition of any one of $R^1$ to $R^7$ and X.

The invention has discovered that the metal-ligand complex of formula (I) having a preferred combination of $R^1$ and $R^7$ groups, in combination with M that is a Group 4 metal, and more preferably hafnium, is particularly valuable for polymerizing olefin monomers comprising ethylene and an alpha-olefin (i.e., copolymerizaing) to prepare a poly(ethylene alpha-olefin) copolymer. Preferably at least $R^1$ is $(C_1-C_{40})$hydrocarbyl, $(C_1-C_{40})$heterohydrocarbyl, $(C_1-C_{40})$hydrocarbyl-O—, or halogen atom, and more preferably $(C_1-C_{40})$hydrocarbyl; and $R^7$ is a $(C_1-C_{40})$hydrocarbyl, preferably a $(C_6-C_{40})$hydrocarbyl, and more preferably a $(C_6-C_{40})$aryl.

In some embodiments the metal-ligand complex of formula (I) is a metal-ligand complex of formula (Ip):

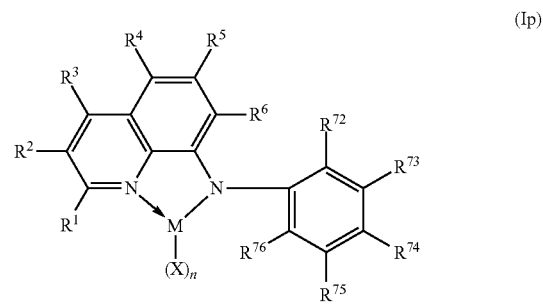

(Ip)

wherein:

At least one of $R^{72}$ and $R^{76}$ independently is a $(C_1-C_{40})$alkyl and each of the remainder of $R^{72}$ to $R^{76}$ independently is a hydrogen atom or $R^S$, and M, n, $R^1$ to $R^6$ and $R^S$ are as defined previously for formula (I).

In some embodiments the metal-ligand complex of formula (I) is a metal-ligand complex of formula (Ia):

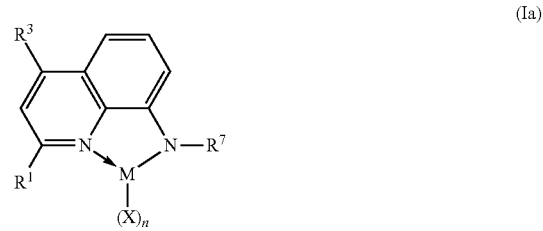

(Ia)

wherein X, n, $R^1$, $R^3$, and $R^7$ are as defined previously. Preferably in formula (Ia), $R^1$ is not a hydrogen atom but is otherwise as defined previously for formula (I).

In some embodiments the metal-ligand complex of formula (Ia) is a metal-ligand complex of formula (Ia-1):

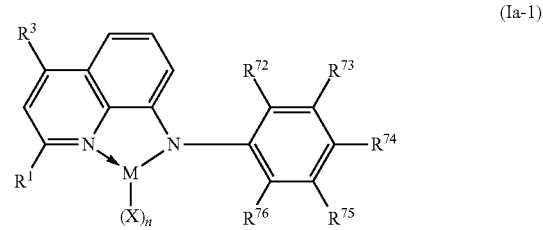

(Ia-1)

wherein each of $R^{72}$ to $R^{76}$ independently is a hydrogen atom or $R^S$, wherein $R^S$ is as defined previously. Preferably at least $R^{72}$, and more preferably at least $R^{72}$ and $R^{76}$ independently is $R^S$, more preferably unsubstituted ($C_1$-$C_{18}$)alkyl, still more preferably unsubstituted ($C_1$-$C_{12}$)alkyl, and even more preferably ($C_1$-$C_6$)alkyl.

In some embodiments the metal-ligand complex of formula (Ia-1) is a metal-ligand complex of formula (Ia-1.1):

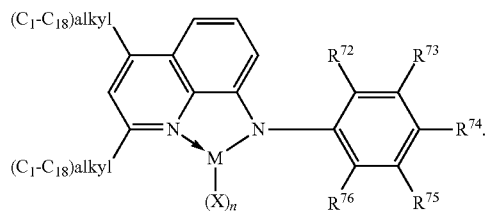

(Ia-1.1)

In some embodiments the metal-ligand complex of formula (Ia-1) is a metal-ligand complex of formula (Ia-1.2):

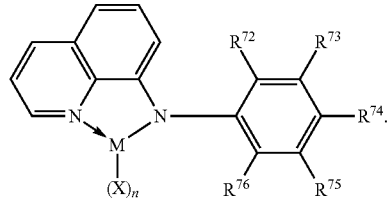

(Ia-1.2)

As shown later in the Examples, the invention has discovered that the metal-ligand complex of formula (Ia-1), especially (Ia-1.2), and more especially (Ia-1.1), in combination with M that is a Group 4 metal, and more preferably hafnium, is particularly valuable for copolymerizaing ethylene and an alpha-olefin to prepare a poly(ethylene alpha-olefin) copolymer. Also still more preferred is the metal-ligand complex of formula (I) of any one of the Examples described later. In some embodiments, the metal-ligand complex of formula (I) is any one of the metal-ligand complexes (5) to (8) and (10) of respective Examples 5 to 8 and 10 described later.

Preferably, the poly(ethylene alpha-olefin) copolymer is characterizable as having a melting temperature ($T_m$) of greater than 60 degrees Celsius, and more preferably greater than 80° C., as determined by differential scanning calorimetry (DSC) using the procedure described later. In some embodiments the melting temperature is a temperature range having end points that are any two of the $T_m$ of the polyolefins of Examples F1 to F8, described later. In some embodiments the poly(ethylene alpha-olefin) copolymer is characterizable as having a weight average molecular weight ($M_w$) in a range having end points that are any two of the $M_w$ values of the polyolefins of Examples F1 to F8, described later. In some embodiments the poly(ethylene alpha-olefin) copolymer is characterizable as having a number average molecular weight ($M_n$) in a range having end points that are any two of the $M_n$ values of the polyolefins of Examples F1 to F8, described later. In some embodiments the poly(ethylene alpha-olefin) copolymer is characterizable as having a polydispersity index (PDI; $M_w/M_n$) in a range having end points that are any two of the PDI values of the polyolefins of Examples F1 to F8, described later. In some embodiments the poly(ethylene alpha-olefin) copolymer is characterizable as having a weight percent (wt %) incorporation of the alpha-olefin (weight of alpha-olefin consumed divided by weight of the poly(ethylene alpha-olefin) copolymer, expressed as a percent) in a range having end points that are any two of the wt % 1-octene incorporation values of the polyolefins of Examples F1 to F8, described later. In some embodiments the poly(ethylene alpha-olefin) copolymer is characterizable as having a mole percent (mol %) vinyl groups (i.e., —CH=$CH_2$ groups). The term "mole percent vinyl groups" means concentration of vinyl groups in the polyolefin expressed as vinyls per 1000 carbon atoms and is determined by proton nuclear magnetic resonance according to the method described later. Preferably the mol % vinyl groups is in a range having end points that are any two of the mol % vinyls values of the polyolefins of Examples F1 to F8, described later.

In some embodiments the invention process employing the metal-ligand complexes of formula (I), especially the metal-ligand complexes of formula (Ia-1.1), and invention catalysts comprising or prepared from same advantageously prepares a polyolefin, especially the poly(ethylene alpha-olefin) copolymer having a desirable high degree of compositional homogeneity. Poly(ethylene alpha-olefin) copolymers having high degrees of compositional homogeneity are useful in applications such as films, especially for use in applications requiring good optical clarity, low haze, or both. The compositional homogeneity can be characterized by DSC on the poly(ethylene alpha-olefin) copolymer according to a DSC method described later. In one DSC measurement indicating compositional homogeneity, the DSC measurement reports heat flow (Watts per gram (W/g)) versus temperature (° C.) curves (cooling or heating curves) that independently exhibit single temperature peaks corresponding to crystallization and melting transitions, respectively. (In contrast DSC curves for poly(ethylene alpha-olefin) copolymer having a low degree of compositional homogeneity exhibit multiple (i.e., 2 or more) temperature peaks, a broad single peak, or a single peak partially overlapped with additional peak(s) appearing as one or more so-called "shoulders.") To use DSC to characterize compositional homogeneity, obtain heating and cooling DSC curves and temperature of crystallization ($T_c$) values from the DSC cooling curve according to the DSC method described later in Materials and Methods. While either the DSC heating or cooling curve can be used to quantify degree of compositional homogeneity, preferably the single peak in the DSC cooling curve is used. The single peak in the DSC cooling curve is characterizable by a full width at half maximum peak height in degrees Celsius ($W_{1/2(DSC)}$) corresponding to a crystallization transition (i.e., $T_c$) from the DSC cooling curve. This measurement is useful for characterizing compositional homogeneity for samples having crystallization transition temperature (i.e., $T_c$) of 60° C. or higher. Generally, width of the peaks in a DSC cooling curve, and thus the $W_{1/2(DSC)}$ value, varies, at least in part, with $T_c$. Lower $W_{1/2(DSC)}$ values reflect higher degrees of compositional homogeneity. In embodiments where $T_c$ is greater than 100° C., preferably $W_{1/2(DSC)}$ is less than or equal to 4.0° C. In embodiments where $T_c$ is from 60° C. to 100° C., preferably $W_{1/2(DSC)}$ is less than or equal to 5.0° C. Another DSC measurement indicating compositional homogeneity is a multiplication (*) product of $T_c$ times $W_{1/2(DSC)}$. Lower $T_c*W_{1/2(DSC)}$ values reflect higher degrees of compositional homogeneity. In some embodiments $T_c*W_{1/2(DSC)}$ is less than 500 degrees Celsius squared (° $C.^2$), and more preferably less than 400° $C.^2$.

The compositional homogeneity of the poly(ethylene alpha-olefin) copolymer can also be characterized by a narrow molecular weight distribution (MWD) as indicated by the aforementioned polydispersity index (PDI; $M_w/M_n$). Lower PDI values indicate higher degrees of compositional homogeneity, that is a smaller range of distribution of chain lengths.

In these preferred embodiments the PDI is less than 3.0, and more preferably less than 2.5, wherein PDI is determined according to a PDI procedure described later. The narrow MWD can be observed by gel permeation chromatography (GPC) on the poly(ethylene alpha-olefin) copolymer according to a GPC method described later. The molecular weight homogeneity can also be characterized by a combination of the aforementioned single DSC peaks and a PDI of less than 3.0, and more preferably less than 2.5.

Still more preferably the poly(ethylene alpha-olefin) copolymer also is characterizable by the aforementioned low levels of vinyl groups. Lower mol % vinyl groups values reflect higher degrees of compositional homogeneity. In some embodiments the mol % vinyl groups is less than 0.10 mol %, preferably less than 0.04 mol %, and more preferably less than 0.03 mol %.

Even more preferably the invention process is one producing such preferred poly(ethylene alpha-olefin) copolymers wherein the catalyst employed in the process is characterizable by a high catalyst efficiency (e.g., greater than 200,000 g copolymer/g metal (M) of metal-ligand complex). Yet more preferably the invention process is one producing such preferred poly(ethylene alpha-olefin) copolymers wherein such preferred poly(ethylene alpha-olefin) copolymers are characterizable by high weight average molecular weight ($M_w$) (>500,000 g/mol, more preferably >600,000 g/mol, still more preferably >800,000 g/mol, and even more preferably >900,000 g/mol); or number average molecular weight ($M_n$) (>170,000 g/mol, more preferably >200,000 g/mol, still more preferably >250,000 g/mol, and even more preferably >300,000 g/mol); or is capable of preparing such preferred poly(ethylene alpha-olefin) copolymers at a reaction mixture temperature of 120° C. or 135° C. using respective conditions as described later in the Examples, especially conditions of Example F1 for 120° C. and conditions of Example E of 135° C.

Even more the poly(ethylene alpha-olefin) copolymer is characterizable by a combination of any two or more of the aforementioned relevant characteristics in the five immediately preceding paragraphs. In some embodiments the combination comprises a PDI of less than 3.0; single peaks observed in both DSC heating and cooling curves; and $W_{1/2 (DSC)}$ less than 5.0° C. In some embodiments the combination comprises a PDI of less than 2.5; single peaks observed in both DSC heating and cooling curves; $W_{1/2(DSC)}$ less than 4.0° C.; and mol % vinyls less than 0.03 mol %. In some embodiments the combination comprises a PDI of less than 3.0; single peaks observed in both DSC heating and cooling curves; and $T_c*W_{1/2(DSC)}$ less than 500° C.$^2$. In some embodiments the combination comprises a PDI of less than 2.5; single peaks observed in both DSC heating and cooling curves; $T_c*W_{1/2(DSC)}$ less than 400° C.$^2$; and mol % vinyls less than 0.03 mol %. In some embodiments the poly(ethylene alpha-olefin) copolymer having the high degree of compositional homogeneity indicated by these combinations is also characterizable by a $M_w$ greater than 600,000 g/mol.

In some embodiments, the invention catalyst comprises, or is prepared from, a preferred metal-ligand complex of formula (I) and a preferred activating co-catalyst, or a reaction product thereof. In other embodiments, the invention catalyst comprises, or is prepared from, two or more preferred metal-ligand complexes of formula (I), and at least one preferred activating co-catalyst, or a reaction product thereof.

In some embodiments the ligand of formula (Q) corresponds to the metal-ligand complex of formula (Ia) or (Ib) or (Ip) (i.e., is a ligand of formula (Qa) or (Qb) or (Qp), respectively, wherein M and Xs have been deleted and H has been added to the nitrogen atom bonded to R$^7$). Preferably in the metal-ligand complex of formula (Ip) and the ligand of formula (Qp) each of R$^{72}$ and R$^{76}$ independently is a ($C_1$-$C_{40}$) alkyl. In some embodiments the invention is the Group 1 or 2 metal salt of the ligand of formula (Qp). The Group 1 or 2 metal salt includes monometal salts and hemimetal salts. Examples the monometal salt are Na(monodeprotonated Q) and [CaOH] (monodeprotonated Q). Examples of the hemimetal salts are Ca(dideprotonated Q)$_2$ and Mg(dideprotonated Q)$_2$. The Group 1 or 2 metal salt of the ligand of formula (Q) can be prepared by contacting the ligand of formula (Q) with about one mole equivalent of a corresponding Group 1 or 2 metal base such as, for example, a Group 1 or 2 metal alkoxide, Group 1 or 2 metal hydroxide, Group 1 or 2 metal bicarbonate, or Group 1 or 2 metal carbonate, preferably in a polar aprotic solvent (e.g., dimethylformamide, dimethylsulfoxide, acetone, or a mixture thereof), polar protic solvent (e.g., methanol, water, or a mixture thereof), or a mixture thereof. Alternatively the Group 1 or 2 metal salt can be directly prepared in situ without going through the conjugate acid that is the ligand of formula (Q).

In some embodiments, the invention catalyst further comprises one or more solvents, diluents (described later), or a combination thereof, as described herein. In other embodiments, the invention catalyst still further comprises a dispersant, e.g., an elastomer, preferably dissolved in the diluent. In these embodiments, the invention catalyst preferably comprises a homogeneous catalyst.

The metal-ligand complexes of formula (I) are rendered catalytically active by contacting them to, or combining them with, an activating co-catalyst or by using an activating technique such as those that are known in the art for use with metal (e.g., a Group 4 metal) olefin polymerization reactions. The present invention contemplates replacing one or more of the activating co-catalysts with the activating technique, although use of activating co-catalysts is preferred. Suitable activating co-catalysts for use herein include alkyl aluminums; polymeric or oligomeric alumoxanes (also known as aluminoxanes); neutral Lewis acids; and non-polymeric, non-coordinating, ion-forming compounds (including the use of such compounds under oxidizing conditions). A suitable activating technique is bulk electrolysis (explained in more detail hereinafter). Combinations of one or more of the foregoing activating co-catalysts and techniques are also contemplated. The term "alkyl aluminum" means a monoalkyl aluminum dihydride or monoalkylaluminum dihalide, a dialkyl aluminum hydride or dialkyl aluminum halide, or a trialkylaluminum. Aluminoxanes and their preparations are known at, for example, U.S. Pat. No. 6,103,657. Examples of preferred polymeric or oligomeric alumoxanes are methylalumoxane, triisobutylaluminum-modified methylalumoxane, and isobutylalumoxane.

Preferred Lewis acid activating co-catalysts are Group 13 metal compounds containing from 1 to 3 hydrocarbyl substituents as described herein. More preferred Group 13 metal compounds are tri(hydrocarbyl)-substituted-aluminum or tri(hydrocarbyl)-boron compounds, still more preferred are tri(($C_1$-$C_{10}$)alkyl)aluminum or tri(($C_6$-$C_{18}$)aryl)boron compounds and halogenated (including perhalogenated) derivatives thereof, even more especially tris(fluoro-substituted phenyl)boranes, still even more especially tris(pentafluorophenyl)borane.

Preferred combinations of neutral Lewis acid activating co-catalysts include mixtures comprising a combination of a tri(($C_1$-$C_4$)alkyl)aluminum and a halogenated tri(($C_6$-$C_{18}$)aryl)boron compound, especially a tris(pentafluorophenyl) borane. Also preferred are combinations of such neutral Lewis acid mixtures with a polymeric or oligomeric alumoxane, and combinations of a single neutral Lewis acid, especially tris(pentafluorophenyl)borane with a polymeric or oligomeric alumoxane. Preferred ratios of numbers of moles of (metal-ligand complex):(tris(pentafluoro-phenylborane): (alumoxane) [e.g., (Group 4 metal-ligand complex):(tris (pentafluoro-phenylborane):(alumoxane)] are from 1:1:1 to 1:10:30, more preferably from 1:1:1.5 to 1:5:10.

Many activating co-catalysts and activating techniques have been previously taught with respect to different metal-ligand complexes in the following U.S. Pat. Nos. 5,064,802; 5,153,157; 5,296,433; 5,321,106; 5,350,723; 5,425,872; 5,625,087; 5,721,185; 5,783,512; 5,883,204; 5,919,983; 6,696,379; and 7,163,907. Examples of suitable hydrocarbyloxides are disclosed in U.S. Pat. No. 5,296,433. Examples of suitable Bronsted acid salts for addition to polymerization catalysts are disclosed in U.S. Pat. Nos. 5,064,802; ; 5,783, 512. Examples of suitable salts of a cationic oxidizing agent and a non-coordinating, compatible anion as activating co-catalysts for addition polymerization catalysts are disclosed in U.S. Pat. No. 5,321,106. Examples of suitable carbenium salts as activating co-catalysts for addition polymerization catalysts are disclosed in U.S. Pat. No. 5,350,723. Examples of suitable silylium salts as activating co-catalysts for addition polymerization catalysts are disclosed in U.S. Pat. No. 5,625,087. Examples of suitable complexes of alcohols, mercaptans, silanols, and oximes with tris(pentafluorophenyl) borane are disclosed in U.S. Pat. No. 5,296,433. Some of these catalysts are also described in a portion of U.S. Pat. No. 6,515,155 B1 beginning at column 50, at line 39, and going through column 56, at line 55, only the portion of which is incorporated by reference herein.

In some embodiments, one or more of the foregoing activating co-catalysts are used in combination with each other. An especially preferred combination is a mixture of a tri(($C_1$-$C_4$)hydrocarbyl)aluminum, tri(($C_1$-$C_4$)hydrocarbyl)borane, or an ammonium borate with an oligomeric or polymeric alumoxane compound.

The ratio of total number of moles of one or more metal-ligand complexes of formula (I) to total number of moles of one or more activating co-catalyst is from 1:10,000 to 100:1. Preferably, the ratio is at least 1:5000, more preferably at least 1:1000; and 10:1 or less, more preferably 1:1 or less. When an alumoxane alone is used as an activating co-catalyst, preferably the number of moles of the alumoxane that are employed is at least 100 times the number of moles of the metal-ligand complex of formula (I). When tris(pentafluorophenyl)borane alone is used as an activating co-catalyst, preferably the number of moles of the tris(pentafluorophenyl)borane that are employed to the total number of moles of one or more metal-ligand complexes of formula (I) form 0.5:1 to 10:1, more preferably from 1:1 to 6:1, still more preferably from 1:1 to 5:1. The remaining activating co-catalysts are generally employed in approximately mole quantities equal to the total mole quantities of one or more metal-ligand complexes of formula (I).

In some embodiments, the invention catalyst further comprises, or is further prepared from, an inorganic or organic particulated solid support, wherein the invention catalyst is in supporting operative contact with the particulated solid support to give an invention particulated solid-supported catalyst. In these embodiments, the invention particulated solid-supported catalyst comprises a heterogeneous catalyst.

The particulated solid support is any material that is capable of supporting the invention catalyst and allows the resulting invention particulated solid-supported catalyst to catalyze polymerization of a polymerizable olefin. Examples of particulated solids are silica, silica gel, alumina, clays, expanded clays (aerogels), aluminosilicates, trialkylaluminum compounds, and organic or inorganic polymeric materials, especially polyolefins such as, for example, a poly(tetrafluoroethylene). More preferably, the invention catalyst and solid support are employed in the invention particulated solid-supported catalyst in amounts that provide a ratio of (weight of the invention catalyst (based on metal $M^1$)):weight of the solid support) of from $1:10^6$ to $1:10^3$, more preferably from $1:10^6$ to $1:10^4$.

In some embodiments, the metal-ligand complexes of this invention (i.e., metal-ligand complexes of formula (I)) are supported on a solid support as described herein and used in olefin polymerization processes in a slurry or a gas phase polymerization. As a practical limitation, slurry polymerization preferably takes place in liquid diluents in which the polymer product is substantially insoluble (e.g., less than 50 milligrams of polymer product dissolves in 1.0 milliliter of liquid diluent at 25° C.). Preferably, the diluent for slurry polymerization is one or more hydrocarbons, each with less than 5 carbon atoms. In some embodiments, one or more saturated hydrocarbons such as ethane, propane or butane are used in whole or part as the diluent. In other embodiments, an alpha-olefin monomer or a mixture of different alpha-olefin monomers are used in whole or part as the diluent. Most preferably, at least a major part of the diluent comprises the alpha-olefin monomer or monomers to be polymerized. In some embodiments, a dispersant, particularly an elastomer, is dissolved in the diluent, preferably utilizing techniques known in the art.

In some embodiments, suspension, solution, slurry, gas phase, solid state powder polymerization or other process conditions are employed. In other embodiments, a particulated solid support is employed in the form of the invention particulated solid-supported catalyst described previously, preferably when the invention particulated solid-supported catalysts are used in an aspect of the first embodiment comprising a gas phase polymerization process. In most polymerization reactions of the first embodiment, the ratio of (moles of invention catalyst):(total moles of polymerizable compounds employed) is from $10^{-12}:1$ to $10^{-1}:1$, more preferably from $10^{-9}:1$ to $10^{-5}:1$.

As previously mentioned, the present invention contemplates a process of preparing the invention catalysts, i.e., rendering one or more metal-ligand complexes of formula (I) catalytically active. The invention catalysts may be made by adapting any relevant process known in the art and the particular process is not critical to the present invention. Preferably, the invention catalyst is prepared by contacting the metal-ligand complex of formula (I) to an activating co-catalyst and a solvent, preferably an aprotic solvent, under conditions sufficient to produce the invention catalyst. Preferably, the conditions sufficient to produce the invention catalyst include those described above for the process of the first embodiment. Preferably, the invention catalyst is prepared in situ. More preferably, the invention catalyst is prepared in situ and used in the process of the first embodiment. In some embodiments, the invention catalyst is prepared in situ in the presence of at least one polymerizable olefin, and the invention catalyst is thereby immediately contacted to the at least one polymerizable olefin in the process of the first embodiment.

In some embodiments, the invention catalyst is prepared as a homogeneous catalyst by addition of one or more metal-ligand complexes of formula (I) and one or more activating co-catalysts to a solvent or diluent in which the polymerization process of the first embodiment will be conducted.

In other embodiments, the invention catalyst is a solid-supported catalyst that is prepared as a heterogeneous catalyst by adsorbing, depositing or chemically attaching one or more metal-ligand complexes of formula (I) and optionally one or more activating co-catalysts on an inorganic or organic particulated solid support to give the invention particulated solid-supported catalyst described herein. In some embodiments, the metal-ligand complex(es) is(are) added to the solid support either subsequently, simultaneously to, or prior to addition of the activating co-catalyst(s) to the solid support. In a preferred embodiment, the invention heterogeneous catalyst is prepared by reacting an inorganic solid support, preferably a tri(($C_1$-$C_4$)alkyl)aluminum compound, with an activating co-catalyst. Preferably, the activating co-catalyst is an ammonium salt of a hydroxyaryl(tris(pentafluorophenyl))borate, more preferably an ammonium salt of either (4-hydroxy-3,5-ditertiarybutylphenyl)tris(pentafluorophenyl)borate or (4-hydroxyphenyl)-tris(pentafluorophenyl)borate. Preferably, the activating co-catalyst is deposited onto the solid support by co-precipitating, imbibing, spraying, or a similar technique, and thereafter any solvent or diluent are preferably removed.

The invention catalysts, whether or not supported on a solid support, preferably are used to polymerize a polymerizable olefin, or co-polymerize two or more polymerizable olefins (i.e., olefin monomers), to prepare a polyolefin. The terms "olefin monomer" and "polymerizable olefin" are synonymous and mean a carbon-carbon double or triple bond-containing monomer or carbon-carbon double or triple bond-containing oligomer or polyolefin prepared therefrom that independently has from 2 to 100,000 carbon atoms, preferably 50,000 carbon atoms or less, more preferably 10,000 carbon atoms or less. Preferably there is at least one carbon-carbon double bond in the polymerizable olefin, and more preferably the polymerizable olefin is a carbon-carbon double bond-containing monomer. Thus, polymerizable olefins include long chain macromolecular alpha-olefin units that are vinyl terminated polymeric remnants formed in situ during continuous solution polymerization reactions. In some aspects of the first embodiment, such long chain macromolecular alpha-olefin units are readily polymerized along with ethylene and other short chain olefin monomers to give a polyolefin having long chain branching.

The term "olefin-polymerizing conditions" means reaction parameters such as, for example, temperature, pressure, concentration of olefin monomer(s), solvent(s), if any, reaction time, and reaction atmosphere sufficient to produce at least 5 mole percent yield of a polyolefin therefrom. In some embodiments polymerization of olefin monomers is accomplished using known conditions for Ziegler-Natta or Kaminsky-Sinn type olefin polymerization reactions. As the process of the first embodiment occurs under olefin-polymerizing conditions sufficient to polymerize at least some of at least one olefin monomer (i.e., polymerizable olefin) and produce a polyolefin therefrom. The process can be performed at or with any temperature, pressure, or other condition (e.g., solvent, atmosphere, and absolute and relative amounts of ingredients) at which the polymerization reaction occurs. Preferably the olefin-polymerizing conditions comprise a temperature of from about −100° C. to about 300° C., more preferably at least about 0° C., still more preferably at least about 20° C., even more preferably at least about 50° C.; and more preferably about 250° C. or less, still more preferably about 200° C. or less, still more preferably about 150° C. or less. In some embodiments, the temperature is at least 30° C., and more preferably at least 40° C. One of the advantages of the invention catalysts is that they functional well at high polymerization temperatures (e.g., more than 130° C.). In some embodiments the temperature is at least 100° C. In some embodiments, the temperature is at least 120° C. In some embodiments, the temperature is at least 130° C. In some embodiments, the temperature is at least 150° C. In some embodiments, the temperature is 200° C. or lower. In some embodiments, the temperature is 180° C. or lower. In some embodiments, the temperature is 160° C. or lower. A convenient temperature is from about 120° C. to about 190° C. (e.g., 135° C.). In some embodiments the olefin-polymerizing conditions comprise a pressure from about 0.5 atmosphere (50 kilopascals (kPa)) to 10,000 atmospheres (1,010,000 kPa), more preferably at least about 1 atmosphere (101 kPa), still more preferably at least about 10 atmospheres (1010 kPa); and more preferably 1000 atmospheres (101,000 kPa) or less, still more preferably 500 atmospheres (50,500 kPa) or less; preferably under a substantially inert atmosphere (e.g., a dry (i.e., substantially free from water) atmosphere consisting essentially of nitrogen gas, a noble gas (e.g., argon gas and helium gas), or a mixture of two or more thereof); with mixing (e.g., agitating, stirring, or shaking) for a time sufficient to produce the polyolefin (e.g., as determined by assaying an aliquot of a reaction mixture).

In some embodiments, the process of the first embodiment employs one or more of the invention catalysts and at least one additional homogeneous or heterogeneous polymerization catalyst, which may be the same as or different than the invention catalyst or may be a prior art olefin polymerization catalyst such as that referenced previously, either in the same reactor or in separate reactors, preferably connected in series or in parallel, to prepare polymer blends having desirable properties. A general description of such a process is disclosed in PCT International Patent Application Publication Number WO 94/00500.

In some embodiments, the polymerization process of the first embodiment is carried out as a batchwise or a continuous polymerization process. A continuous process is preferred, in which continuous process, for example, invention catalyst, ethylene, a co-monomer olefin other than ethylene, and optionally a solvent, diluent, dispersant, or combination thereof are essentially continuously supplied to the reaction zone, and resulting polyolefin product is essentially continuously removed therefrom.

Preferably, such polyolefin products are produced in a solution process, most preferably a continuous solution process. Without limiting in any way the scope of the invention, an illustrative means for carrying out such an essentially continuous polymerization process is as follows. In a stirred-tank reactor, the monomer olefins to be polymerized are introduced continuously, together with solvent and an optional chain transfer agent such as, for example, a stream of hydrogen introduced to the reactor. The reactor contains a liquid phase composed substantially of monomers, together with any solvent or additional diluent and dissolved polymer. In other embodiments, a small amount of a "H"-branch-inducing diene such as norbornadiene, 1,7-octadiene, or 1,9-decadiene is also added. Metal-ligand complex of formula (I) and activating co-catalyst are continuously introduced in the reactor liquid phase. In some embodiments, reactor temperature and pressure are controlled by, for example, adjusting solvent/monomer ratio, adjusting addition rates, cooling or heating the reactor liquid phase (e.g., using coils, jackets or both), or a combination thereof. In some embodiments, rate of polymerization is controlled by adjusting rate of addition of the invention catalyst. In some embodiments, ethylene content of a polymer product thereof is varied by adjusting the ratio of ethylene to comonomer olefin in the reactor, which ratio preferably is controlled by manipulating the respective feed rates of the monomers to the reactor. In some embodiments, molecular weight of polymer product is controlled by adjusting temperature, adjusting monomer concentration, or with the previously mentioned chain transfer agent. In some embodiments, reactor effluent is contacted with a catalyst kill agent such as water. A resulting polyolefin product solution is optionally heated, and the polyolefin is recovered by devolatilizing, e.g., flashing off volatiles such as gaseous monomers, residual solvent, and diluents at reduced pressure. In some embodiments, further devolatilization is conducted in equipment such as a devolatilizing extruder. In a continuous process, mean residence time of the invention catalyst and polyolefin product in the reactor preferably is from about 5 minutes to about 8 hours, and more preferably from about 10 minutes to about 6 hours.

Generally the ethylene/alpha-olefin copolymers have densities from 0.85 grams per milliliter (g/mL) to 0.96 g/mL. In some embodiments, a comonomer-to-monomer ratio of moles of alpha-olefin comonomer to moles of ethylene monomer used in the polymerization is varied in order to adjust the density of the resulting ethylene/alpha-olefin copolymer. When producing ethylene/alpha-olefin copolymers with a preferred density range of from 0.91 g/mL to 0.93 g/mL, preferably the comonomer-to-monomer ratio is less than 0.2, more preferably less than 0.05, still more preferably less than 0.02, and even more preferably less than 0.01. In some embodiments, use of hydrogen gas has been found to effectively control the molecular weight of the resulting ethylene/alpha-olefin copolymer. In some embodiments, the ratio of moles of hydrogen gas to moles of monomer is less than about 0.5, preferably less than 0.2, more preferably less than 0.05, still more preferably less than 0.02 and even more preferably less than 0.01.

Preferably, each olefin monomer (i.e., polymerizable olefin) independently is ethylene; a linear or branched alpha-olefin of from about 3 to about 20 carbon atoms such as, for example, propylene, isobutylene, 1-butene, 1-pentene, 1-hexene, 3-methyl-1-pentene, 4-methyl-1-pentene, 1-octene, 1-decene, long chain macromolecular α-olefins, and mixtures thereof; an acyclic diene such as, for example, 1,4-butadiene, 1,4-hexadiene, and 1,7-octadiene; a cyclic olefin such as, for example, cyclobutene, cyclopentene, norbornene, and norbornene derivatives that are substituted in the 5- and 6-positions with $(C_1-C_{20})$hydrocarbyl groups; a cyclic diene hydrocarbon of from about 4 to about 40 carbon atoms such as, for example, a cyclohexadiene, ethylidene-norbornene, and norbornadiene; an aromatic ring-substituted olefin of from 8 to 20 carbon atoms (e.g., styrene, $(C_1-C_4)$alkyl-substituted styrenes, and 4-phenylbutene); a vinyl monomer that is, for example, 4-vinylcyclohexene, divinylbenzene, and mixtures thereof with ethylene, an acrylonitrile, maleic acid ester, vinyl acetate, acrylate ester, methacrylate ester, or vinyl trialkyl silane; and mixtures thereof such as mixtures of ethylene and styrene, mixtures of ethylene, propylene, and styrene; mixtures of ethylene, styrene or propylene, and 1,4-hexadiene or a non-conjugated diene, especially ethylidene-norbornene.

As mentioned previously, the present invention contemplates a process of preparing the metal-ligand complex of formula (I). Metal-ligand complexes of formula (I) may be made by adapting any relevant process known in the art and the particular process is not critical to the present invention. The metal-ligand complex of formula (I) may exist as an isolated crystal(s), optionally being in substantially pure form (i.e., greater than 90%), or as a mixture with one or more other metal-ligand complexes of formula (I); in the form of a solvated adduct, optionally in a solvent, especially an organic liquid, preferably an aprotic solvent; in the form of a dimer; or in the form of a chelated derivative thereof, wherein the chelated derivative comprises the metal-ligand complex of formula (I) and a chelating agent. Preferably, the chelating agent is an organic Lewis base (e.g., an aprotic organic solvent such as tetrahydrofuran (THF) or an aprotic amine base such as triethylamine).

In some embodiments, a reducing agent is also employed (either in a synthesis of the metal-ligand complex of formula (I) or preparation of the invention catalyst therefrom) so as to produce lower oxidation state forms (e.g., +2) of the metal-ligand complexes of formula (I) from higher oxidation state forms (e.g., +4) of the metal-ligand complexes of formula (I). As used herein, the term "reducing agent" means a metal-containing substance or compound, organic reductant, or technique (e.g., electrolysis) which, under reducing conditions, causes the metal, $M^1$, to be reduced from a higher to a lower oxidation state (e.g., from a +6 formal oxidation state to a +4 formal oxidation state). Examples of suitable reducing agents are alkali metals, alkaline earth metals, aluminum and zinc, and alloys of alkali metals or alkaline earth metals such as sodium/mercury amalgam and sodium/potassium alloy. Examples of other suitable reducing agents are sodium naphthalenide, potassium graphite, lithium alkyls, lithium or potassium alkadienyls, and Grignard reagents (e.g., alkyl magnesium halides). Most preferred reducing agents are the alkali metals or alkaline earth metals, especially lithium and magnesium metal. Suitable techniques that may be adapted by an ordinarily skilled artisan for preparing the metal-ligand complexes of the present invention are known and preferably are derived from techniques taught, for example, in U.S. Pat. Nos. 5,866,704; 5,959,047; and 6,268,444.

Once prepared, preferably the metal-ligand complex of formula (I) is collected in an isolated form, which means being substantially solvent-free, for example, contains 10 percent by weight or less of a total of any solvent(s) used in a preparation thereof and the metal-ligand complex of formula (I) being at least 70% by weight of the isolated form. Still more preferably, the metal-ligand complex of formula (I) is collected and purified in an isolated and purified form (i.e., the metal-ligand complex of formula (I) being substantially solvent-free and comprising at least 80% by weight, more preferably at least 90% by weight, of the purified form. As used herein, percent by weight is based on the total weight of a form or mixture. Preferably, the weight percent of the metal-ligand complex of formula (I) in such mixtures is determined using 13-carbon or proton nuclear magnetic resonance ($^{13}C$- or $^1H$-NMR, respectively) spectroscopy.

Syntheses of some of the ligands (e.g., a compound formed by removing M and X from formula (I)) employed to prepare the metal-ligand complexes of formula (I) may utilize starting materials, intermediates, or reaction products that contain more than one reactive functional group. During chemical reactions, a reactive functional group may be protected from unwanted side reactions by a protecting group that renders the reactive functional group substantially inert to the reaction conditions employed. A protecting group is selectively introduced onto a starting material or intermediate prior to carrying out the reaction step for which the protecting group is needed. Once the protecting group is no longer needed, the protecting group can be removed. It is well within the ordinary skill in the art to introduce protecting groups during a synthesis and then later remove them. Procedures for introducing and removing protecting groups are known, for example, in Protective Groups in Organic Synthesis, 3rd ed., Greene T. W. and Wuts P. G., Wiley-Interscience, New York, 1999. The following moieties are examples of protecting groups that may be utilized to protect amino, hydroxy), or other functional groups: carboxylic acyl groups such as, for example, formyl, acetyl, and trifluoroacetyl; alkoxycarbonyl groups such as, for example, ethoxycarbonyl, tert-butoxycarbonyl (BOC), β,β,β-trichloroethoxycarbonyl (TCEC), and β-iodoethoxycarbonyl; aralkyloxycarbonyl groups such as, for example, benzyloxycarbonyl (CBZ), para-methoxybenzyloxycarbonyl, and 9-fluorenylmethyloxycarbonyl (FMOC); trialkylsilyl groups such as, for example, trimethylsilyl (TMS) and tert-butyldimethylsilyl (TBDMS); and other groups such as, for example, triphenylmethyl(trityl), tetrahydropyranyl, vinyloxycarbonyl, ortho-nitrophenylsulfenyl, diphenylphosphinyl, para-toluenesulfonyl (Ts), mesyl, trifluoromethanesulfonyl, methoxymethyl (MOM), and benzyl. Examples of procedures for removing protecting groups include hydrogenolysis of CBZ groups using, for example, hydrogen gas at about 3.4 atmospheres in the presence of a hydrogenation catalyst such as 10% palladium on carbon, acidolysis of BOC or MOM groups using, for example, hydrogen chloride in dichloromethane or trifluoroacetic acid (TFA) in dichloromethane, reaction of silyl groups with fluoride ions, and reductive cleavage of TCEC groups with zinc metal.

The invention contemplates preparing the metal-ligand complex of formula (I) and ligands of formula (Q) by any suitable method. The method of preparation is not critical. A preferred process for preparing the metal-ligand complex of formula (I) employs the ligand of formula (Q). The ligand of formula (Q) can be prepared in turn by any one of a number of conventional methods and starting from materials readily synthesizable by a person of ordinary skill in the art or, preferably, starting from commercially available starting materials. Some preferred methods are described below. Preferably the method employs a convergent synthesis approach involving coupling together of two primary intermediates. Preferred illustrative procedures are described below and shown in FIGS. 1 to 4.

An illustrative procedure for preparing a first primary intermediate of formula useful in the convergent synthesis is shown in Scheme 1 in FIG. 1. In Scheme 1, the first primary intermediate is of formula (a2), which preferably is available from a commercial source. The preparation of the first primary intermediate of formula (a2) can be accomplished by converting starting material (a1) having a penultimate moiety T to the primary intermediate of formula (a2) by conventional means. Preferably, T is, for example, a nitro, azido, or hydrazido, all converted via reduction; hydroxyl, acetate, triflate, fluoro, bromo, or iodo, all converted via a substitution reaction (catalyzed or uncatalyzed); phthalimido, imino, isocyanide, or carboxamido, all converted via a hydrolysis; or aminocarbonyl (converted via a Hofmann rearrangement). Preferably starting material (a1) is commercially available. Alternatively in Scheme 1, the preparation of the first primary intermediate of formula (a2) can be accomplished by converting starting material (a3) or (a4) having a moiety $R^{7a}$ to the primary intermediate of formula (a2) by conventional means. Preferably, $R^{7a}$ is, for example, an alkyl, cycloalkyl, or phenyl that undergoes a reaction to form a derivative thereof that is $R^7$. Examples of such reactions are alkylation, halogenation, reduction, oxidation, and substitution. It may be convenient to carry out the conversion of $R^{7a}$ to $R^7$ with a NPG protected —NH$_2$ group as shown with (a4). Preferably, NPG is, for example, phthalimido, dibenzylamino, tertiary-butoxycarbonyl (i.e., a BOC); benzyloxycarbonyl (i.e., a CBZ), or fluorenylmethyloxycarbonyl (i.e., FMOC). The reactions described in Scheme 1 preferably are carried out under a substantially inert gas atmosphere in an anhydrous aprotic solvent such as, for example, diethyl ether, toluene, xylenes, tetrahydrofuran, diethylene glycol dimethyl ether, or a combination thereof and at a temperature in a range of from about −78° C. to about 200° C. Preparation of first primary intermediate (a2) can also be carried out in polar organic solvents such as, for example, acetone, ethyl acetate, acetonitrile, ethanol, a mixture thereof, and water-containing mixtures thereof. Preferably, the reactions are carried out at atmospheric pressure.

Figure 2:
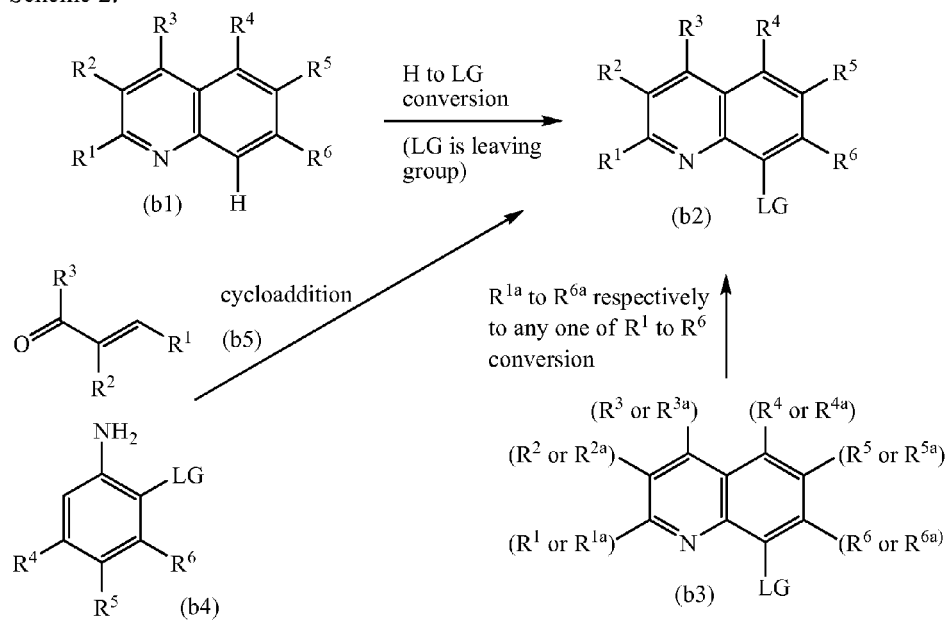
FIG. 2 shows an illustrative procedure of Scheme 2 for preparing a second primary intermediate useful in a convergent synthesis of the ligand of formula (Q).

An illustrative procedure for preparing a second primary intermediate useful in the convergent synthesis is shown in Scheme 2 in FIG. 2. In Scheme 2, the second primary intermediate is of formula (b2), which preferably is available from a commercial source. The preparation of the second primary intermediate of formula (b2) can be accomplished by reacting starting material (b1) with a source LG-Y of a leaving group LG to give functionalized quinoline (b2), wherein LG is, for example, Br or I. The source of the leaving group LG-Y can be, for example, Br$_2$, N-bromosuccinimide (NBS), or I$_2$. Depending on particular $R^1$ to $R^6$ employed in Scheme 2, starting material (b1) is available from commercial suppliers or can be readily prepared by a person of ordinary skill in the art. Alternatively in Scheme 2, preparation of the second primary intermediate of formula (b2) can be accomplished by converting a starting material (b3) having at least one penultimate moiety ($R^{1a}$, $R^{2a}$, $R^{3a}$, $R^{4a}$, $R^{5a}$, or $R^{6a}$) and the remainder being $R^1$ to $R^6$ as defined for formula (I). Preferably, the penultimate moiety is, for example, a hydrogen atom or halogen atom that is replaced by a substituent or an alkyl, cycloalkyl, or phenyl that undergoes a reaction to form a derivative thereof. Examples of such reactions are alkylation, halogenation, reduction, oxidation, and substitution. Not indicated in Scheme 2, preparation of the second primary intermediate of formula (b2) can be accomplished by also converting the starting material (b1) having the at least one penultimate moiety ($R^{1a}$, $R^{2a}$, $R^{3a}$, $R^{4a}$, $R^{5a}$, or $R^{6a}$; not indicated) and the remainder being $R^1$ to $R^6$ as defined for formula (I) before or after the aforementioned introduction of LG. Alternatively in Scheme 2, an aniline (b4) can be reacted with an unsaturated carbonyl-containing compound (b5) that is an unsaturated aldehyde ($R^3$ is H) or ketone ($R^3$ is ($C_1$-$C_{40}$) hydrocarbyl) under cycloaddition conditions (e.g., in presence of a Lewis acid such as anhydrous zinc chloride) to give the second primary intermediate of formula (b2). Not shown in Scheme 2 is still another alternative route employing a saturated analog in place of the unsaturated carbonyl-containing compound (b5) (i.e., wherein the —CH($R^2$)=CHR$^1$ group in (b5) has been replaced in Scheme 2 with —CH$_2$($R^2$)—CH$_2$R$^1$) and, after the cycloaddition reaction, conventionally oxidizing the resulting 3,4-dihydroquinoline intermediate (not shown) to give the second primary intermediate of formula (b2). The reactions described in Scheme 2 preferably are carried out under a substantially inert gas atmosphere in an anhydrous aprotic solvent such as, for example, diethyl ether, toluene, xylenes, tetrahydrofuran, diethylene glycol dimethyl ether, or a combination thereof and at a temperature in a range of from about −78° C. to about 200° C. Preparation of second primary intermediate (b2) can also be carried out in polar organic solvents such as, for example, acetone, ethyl acetate, acetonitrile, ethanol, a mixture thereof, and water-containing mixtures thereof. Preferably, the reactions are carried out at atmospheric pressure.

Figure 3:
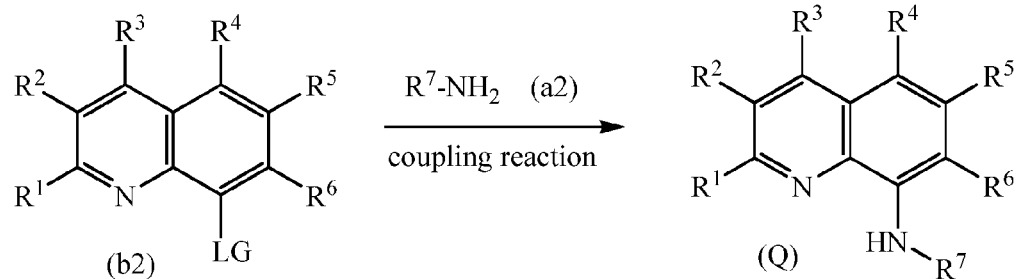
FIG. 3 shows an illustrative procedure of Scheme 3 for preparing the ligand of formula (Q) from the first and second primary intermediates.

An illustrative procedure for preparing the ligand of formula (Q) from the first and second primary intermediates is shown in Scheme 3 in FIG. 3. In Scheme 3, the preparation of the ligand of formula (Q) comprises coupling of first primary intermediate (a2) (prepared as shown in Scheme 1) with second primary intermediate (b2) (prepared as shown in Scheme 2) to give a ligand of formula (Q). The reactions described in Scheme 3 preferably are carried out under coupling conditions such as in the presence of a catalyst (e.g., a palladium catalyst as described later) under a substantially inert gas atmosphere in an anhydrous aprotic solvent such as, for example, dimethylformamide, diethyl ether, toluene, xylenes, tetrahydrofuran, diethylene glycol dimethyl ether, or a combination thereof and at a temperature in a range of from about −78° C. to about 200° C. Preferably, the reactions are carried out at atmospheric pressure. An example of such coupling conditions is so-called Buchwald/Hartwig conditions such as catalytic amounts of palladium(II)acetate and 2,2'-bis(diphenylphosphine)-1,1'-binaphthyl (BINAP), which are premixed; potassium tertiary-butoxide, and dimethylformamide (DMF); microwave under argon gas at 130° C. to 180° C. for 4 minutes. Another example is 2 mole percent (mol %) tris(dibenzylidene acetone)dipalladium(0) ($Pd_2(dba)_3$) and 6 mol % (−)-(R)—N,N-dimethyl-1-[(S)-2-(diphenylphosphino)ferrocenyl]-ethylamine [(R,S)-PPFA], which are premixed; sodium tertiary-butoxide, and toluene; microwave under argon gas at 120° C. for 10 minutes.

Figure 4:
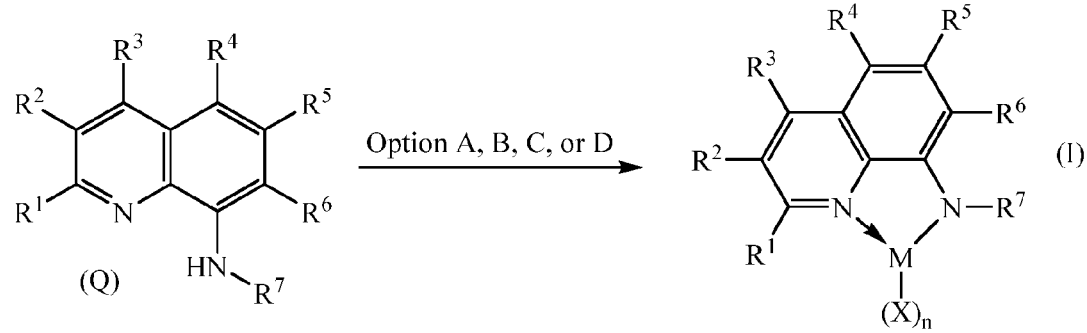
FIG. 4 shows an illustrative procedure of Scheme 4 for preparing the metal-ligand complex of formula (I) from the ligand of formula (Q).

An illustrative procedure for preparing the metal-ligand complex of formula (I) from the ligand of formula (Q) is shown in Scheme 4 in FIG. 4. In Scheme 4, the preparation of the metal-ligand complex of formula (I) involves reacting the ligand of formula (Q) (prepared as shown in Scheme 3) with a source or sources of M and X as shown, for example, in Options A to D. In option A, the compound of formula (Q) is deprotonated with a non-nucleophilic base to give amide anion in situ (not shown), which is then allowed to react with a metal halide such as, for example, $M(Cl)_{n+1}$, wherein M is as defined previously, followed by reaction of the resulting metal-ligand complex with a organometallic compound such as, for example, an organolithium (X—Li) or Grignard reagent (X—MgBr) (or organosodium (X—Na) or organopotassium (X—K)), wherein X is as defined above to give the compound of formula (I). Alternatively in option B, the compound of formula (Q) reacts with a metal-amido compound such as, for example, $M(NR^K R^L)_{n+1}$, wherein $R^K$ and $R^L$ are as defined previously for formula (I) to give an intermediate in situ (not shown), which then reacts with the organometallic compound X—Li or X—MgBr (e.g., organolithium or Grignard reagent) to give the compound of formula (I). In yet another option C, the compound of formula (Q) reacts with an organometallic compound $M(X)_{n+1}$ (or $M(Cl)_{n+2}$) to give the compound of formula (I). In yet another alternative option D, the compound of formula (Q) reacts with the metal halide such as $M(Cl)_{n+1}$ (or $M(Cl)_{n+2}$), followed by reaction of the resulting metal-ligand complex with 3 mole equivalents of an organometallic compound X—Li or X—MgBr such as, for example, methyl lithium or methyl magnesium bromide to give the compound of formula (I). The reactions described in Scheme 4 preferably are carried out under a substantially inert gas atmosphere in an anhydrous aprotic solvent such as, for example, toluene, xylenes, tetrahydrofuran, diethylene glycol dimethyl ether, or a combination thereof and at a temperature in a range of from about −78° C. to about 200° C. Preferably, the reactions are carried out at atmospheric pressure.

The invention contemplates procedures for preparing the metal-ligand complex of formula (I) and ligands of formula (Q) other than the previously described procedures illustrated in FIGS. 1 to 4. Such other procedures would be readily known to one of ordinary skill in the art. Specific non-limiting examples of the previously described procedures illustrated in FIGS. 1 to 4 are given below in the Preparations and Examples.

Materials and Methods

General ethylene/1-octene Copolymerization Procedure.

Pass all feeds through purification columns of alumina and Q-5™ catalyst (available from Englehardt Chemicals Inc.) prior to introduction into the reactor.

Charge a one gallon (3.79 L) stirred autoclave reactor with mixed alkanes solvent (ISOPAR® E (Exxon Mobil Corporation, Irving, Tex., USA); about 1.35 kg) and 1-octene (250 g). Heat the charged reactor to a polymerization reaction temperature (e.g., 120° C. or 135° C.), and charge the heated reactor with hydrogen gas (20.1 mmol) followed by approximately 125 g or 145 g, as the case may be, of ethylene (after it has been passed through the purification columns) to bring total pressure in the reactor to about 425 pounds per square inch gauge (psig) (2.95 megapascals (MPa)). Prepare a catalyst composition in a drybox under inert atmosphere (e.g., nitrogen or argon gas) by mixing together a known amount in moles of a precatalyst (e.g., the metal-ligand complex of formula (I)) with an activating co-catalyst. The activating co-catalyst comprises a mixture of 1.2 mole equivalents of a mixture of methyldi(($C_{14}$-$C_{18}$)alkyl)ammonium salts of tetrakis(pentafluorophenyl)borate, abbreviated herein as MDATPB), prepared by reaction of a long chain trialkylamine (ARMEEN™ M2HT, available from Akzo-Nobel, Inc.), HCl and $Li[B(C_6F_5)_4]$, substantially as disclosed in U.S. Pat. No. 5,919,9883, Ex. 2, and 50 mole equivalents of triisobutylaluminum modified methylalumoxane (MMAO-3A)) with additional mixed alkanes solvent to give a total volume of about 17 mL, the mole equivalents being based on the moles of the precatalyst. Then inject the resulting activated catalyst mixture into the reactor over about 4 minutes by a pump system. Keep polymerization reaction temperature and pressure in the reactor constant by feeding ethylene into it during polymerization and cooling the reactor as needed to give product polymer (e.g., poly(ethylene 1-octene)copolymer). After 10 minutes, shut off the ethylene feed, and transfer the resulting solution into a nitrogen-purged resin kettle. Add an additive toluene solution containing a 2:1 ratio by weight of a phosphorous stabilizer (IRGAFOS™ 168 from Ciba Geigy Corporation) and phenolic antioxidant (IRGANOX™ 1010 from Ciba Geigy Corporation) to give a total additive content of approximately 0.1% in the product polymer. Thoroughly dry the product polymer in a vacuum oven.

Between polymerization runs a wash cycle is conducted in which 850 g of mixed alkanes are added to the reactor and the reactor is heated to 150° C. The reactor is then emptied of the heated solvent immediately before beginning a new polymerization run.

General Considerations.

All solvents are obtained from commercial sources (i.e., Aldrich Chemical Company (Aldrich)) and are dried via passage through columns of alumina, molecular sieves, or both (undried solvents are used for column chromatography). Toluene, hexanes, benzene-$d_6$ ($C_6D_6$), and toluene-$d_8$ are dried and degassed according to known procedures. Nuclear magnetic resonance (NMR) spectra are recorded on Bruker Avance-400 NMR spectrometer. Chemical shifts in parts per million (δ) are reported versus tetramethylsilane and referenced to residual protons in a deuterated solvent. NMR peak and coupling constant assignments are provided for convenience and are not limiting. Some of the atoms in the structures of the Preparations and Examples are numbered for ease of reference. All metal-ligand complexes are synthesized and stored in a Vacuum Atmospheres substantially inert atmosphere glove box under a dry nitrogen atmosphere or by using standard Schlenk and vacuum line techniques. End groups are analyzed by proton-nuclear magnetic resonance ($^1$H-NMR) spectroscopy using the Bruker Avance-400 NMR instrument and deuterated tetrachloroethane. 8-Bromoquinoline is purchased from ArkPharm Inc. 2,4-Dimethyl-8-bromoquinoline is purchased from Princeton BioMolecular Research. Substituted anilines are purchased from Aldrich.

Special techniques are employed to improve the signal-to-noise ratio for the $^1$H and $^{13}$C NMR spectroscopy, respectively.

$^{13}$C-NMR Sample Preparation and Method ($^{13}$C-NMR for Comonomer Content).

Add approximately 2.7 grams (g) of a 50/50 volume/volume mixture of tetrachloroethane-d$_2$/orthodichlorobenzene containing 0.025 molar (M) of tris(acetylacetonato)chromium(III) (Cr(AcAc)$_3$) to a 0.1 g sample of the polymer to be analyzed in a Norell 1001-7 10 millimeter (mm) NMR tube. Dissolve sample and homogenize it by heating the tube and its contents to 150° C. using a heating block and heat gun. Visually inspect each sample to ensure homogeneity.

Data Acquisition Parameters ($^{13}$C).

Aquire NMR data using a 6-second pulse repetition delay, 90 degree flip angles, and inverse gated decoupling with a sample temperature of 120° C. Make all measurements on non-spinning samples in locked mode. Allow samples to thermally equilibrate for 7 minutes prior to the data acquisition. The $^{13}$C NMR chemical shifts are internally referenced to the EEE triad at 30.0 ppm. Data analysis for comonomer content is carried out using the following method:

Comonomer content is determined using the assignments from reference 1 and integrated C13 NMR spectra to solve the vector equation s=fM where M is an assignment matrix, s is a row vector representation of the spectrum, and f is a mole fraction composition vector. The elements of f are taken to be triads of E and O with all permutations of E and O. The assignment matrix M is crated with one row for each triad in f and a column for each of the integrated NMR signals. The elements of the matrix are integral values determined by reference to the assignments in reference 1. The equation is solved by variation of the elements off as needed to minimize the error function between s and the integrated C13 data for each sample.

Reference 1 is XiaoHua Qiu, Zhe Zhou, Gian Gobbi and Oscar D. Redwine, *Error Analysis for NMR Polymer Microstructure Measurement without Calibration Standards*, Anal. Chem., 2009; 81 (20): 8585-8589.

$^1$H-NMR Sample Preparation and Method.

Add 3.26 g of stock solution to 50 milligrams (mg) of polymer sample in 10 mm NMR tube. The stock solution is a mixture of tetrachloroethane-d$_2$ (TCE) and perchloroethylene (50:50, wt:wt) with 0.001M Cr$^{3+}$. The solution in the tube is purged with N$_2$ for 5 minutes to reduce the amount of oxygen and reduce oxidation. The sample tube is left at room temperature overnight to swell the polymer sample, and then the sample is dissolved with the help of a vortexer and a heat block at 110° C.

Run the $^1$H NMR with a 10 mm cryoprobe at 120° C. Two experiments are run to get unsaturation, control and double presaturation experiments. The control is run with ZG pulse, TD 32768, NS 4, DS 12, SWH 10,000 Hz, AQ 1.64s, D$_1$ 14s. The double presaturation experiment is run with a modified pulse sequence using the parameters TD 32768, NS 200, DS 4, SWH 10,000 Hz, AQ 1.64s, D$_1$ 1 s, D$_{13}$ 13s.

To calculate the mol % vinyl groups, signal from residual $^1$H of TCE is set to 100, the integral from 3 ppm to –0.5 ppm is used as the signal from whole polymer in the control experiment. The signal from residual $^1$H of TCE is set to 100 and the corresponding integrals for unsaturations (vinylene, trisubstituted unsaturation, vinyl and vinylidene unsaturations) are obtained in the double presaturation experiment. The integrals for the vinyl unsaturations are used to calculate the mol % vinyl groups, expressed as vinyl groups per 1000 carbon atoms.

Determining Percent Incorporation of 1-octene and Polymer Density by Infrared (IR) Spectroscopy.

Deposit 140 microliters (μL) of each polymer solution onto a silica wafer, heat at 140° C. until the 1,2,4-trichlorobenzne (TCB) evaporates, and analyze using a Nicolet Nexus 670 FT-IR with 7.1 version software equipped with an AutoPro auto sampler.

Gel Permeation Chromatography (GPC).

Unless otherwise noted, determine number and weight-average molecular weights (M$_n$ and M$_w$, respectively) of polymers are determined by GPC. Use a chromatographic system that is either a Polymer Laboratories Model PL-210 or a Polymer Laboratories Model PL-220. Operate column and carousel compartments of the chromatographic system at 140° C. Use three Polymer Laboratories 10-micron Mixed-B columns with a solvent of 1,2,4-trichlorobenzene. Prepare samples at a concentration of 0.1 g of polymer in 50 mL of solvent. The solvent used to prepare the samples contains 200 parts per million (ppm) of butylated hydroxytoluene (BHT). Prepare samples by agitating them lightly for 2 hours at 160° C. Use an injection volume of 100 μL and a flow rate of 1.0 mL/minute. Calibrate the GPC column set with narrow molecular weight distribution (MWD) polystyrene standards purchased from Polymer Laboratories. Convert polystyrene standard peak molecular weights to polyethylene molecular weights using:

$$M_{polyethylene} = A(M_{polystyrene})^B \quad (1)$$

wherein M$_{polyethylene}$ is the molecular weight of the polyethylene, M$_{polystyrene}$ is molecular weight of the polystyrene, A has a value of 0.4316, and B is equal to 1.0. Perform polyethylene equivalent molecular weight calculations using Viscotek TriSEC software Version 3.0.

Density.

Determine polymer densities by liquid displacement (Archimedes Principle) using 2-propanol as solvent in accord with ASTM D792 Method B.

Differential Scanning Calorimetry.

Determining melting and crystallization temperatures and heat of fusion by Differential Scanning calorimetry (DSC; DSC 2910, TA Instruments, Inc.). First heat samples from room temperature to 180° C. at a heating rate of 10° C. per minute. After being held at this temperature for 2 to 4 minutes, cool the samples to –40° C. at a cooling rate of 10° C. per minute; hold the sample at the cold temperature for 2 to 4 minutes, and then heat the sample to 160° C.

Obtain melting temperature (T$_m$) values from the DSC heating curve. Obtain temperature of crystallization (T$_c$) values from DSC cooling curve.

Obtain a width in degrees Celsius that corresponds to the full width at half the maximum height of the peak (W$_{1/2(DSC)}$) corresponding to a crystallization transition (i.e., T$_c$) from the DSC cooling curve. This measurement is useful for characterizing compositional homogeneity for samples having a crystallization transition from the DSC cooling curve that occurs at a temperature (T$_c$) of 60° C. or higher. Multiply T$_c$ times W$_{1/2(DSC)}$ to obtain a multiplication product thereof that is also useful for characterizing compositional homogeneity for the samples.

Abbreviations (meanings): κ (kappa); i-Pr (isopropyl, i.e., 2-propyl); Ph (phenyl); Bn (benzyl); Me (methyl); nBu, n-Bu and the like (normal-butyl); CH$_2$Cl$_2$ (dichloromethane); CD$_2$Cl$_2$ (dichlorodeuteromethane); THF (tetrahydrofuran); p-TsOH.H$_2$O (para-toluenesulfonic acid monohydrate); TiCl$_4$ (titanium(IV)chloride); K$_2$CO$_3$ (potassium carbonate); Me (methyl); C$_6$D$_6$ (perdeuterobenzene); toluene-d$_8$ (perdeuterotoluene); Et$_3$N (triethylamine); ZrBn$_4$ (zirconium tetrabenzyl); HfBn$_4$ and Hf(CH$_2$Ph)$_4$ (hafnium tetrabenzyl); r.t. (room temperature); g (gram(s)); mL (milliliter(s)); ° C. (degrees Celsius); × (times (as in 2×15 mL)); mmol (millimole(s)); psi (pounds per square inch); psig (pounds per square inch gauge); MHz (MegaHertz); Hz (Hertz) m/z (mass-to-charge); $^1$H-NMR (proton NMR); $^{13}$C-NMR (carbon-13 NMR); $^{19}$F-NMR (fluorine-19 NMR); HSQC (heteronuclear single quantum coherence); Anal. (elemental analysis); calcd (calculated); br (broad); sept. (septet); s (singlet); d (doublet); t (triplet); m (multiplet); quat. (quartet); J (coupling constant); HRMS (high resolution mass spectrometry); ESI (electrospray mass spectrometry), GC/MS (CI) (gas chromatography-mass spectrometry chemical ionization); TLC (thin layer chromatography).

Benzyl metals and other organo metals such as alkyl metals and trialkylsilyl metals, wherein the metals are M as defined for formula (I), are useful starting materials for reacting with compounds of formula (Q) to give certain metal-ligand complexes of formula (I). It is not critical how such organo metals are prepared. In some embodiments, such organo metals are prepared starting from a corresponding metal halide (e.g., metal chloride or bromide) or metal alkoxide (e.g., metal tetrabutoxide) and an organo lithium or organo magnesium halide. For example, in some embodiments, such benzyl metals are prepared as described in U.S. Pat. No. 7,067,686 B1. The corresponding metal halides typically are available commercially such as, for example, from the Sigma-Aldrich Company, Saint Louis, Mo., USA and CHEMOS GmbH, Regenstauf, Germany. In other embodiments, such benzyl metals are purchased from a commercial source (for example, CHEMOS GmbH sells tetrabenzylhafnium under catalog number 151655 and tetrabenzylzirconium under catalog number 150405).

Non-limiting examples of the present invention are described below that illustrate some specific embodiments and aforementioned advantages of the present invention. Preferred embodiments of the present invention incorporate one limitation, and more preferably any two, limitations of the Examples, which limitations thereby serve as a basis for amending claims.

EXAMPLES OF THE PRESENT INVENTION

Example 1

Preparation of
N-(2,6-diisopropylphenyl)quinolin-8-amine (1)

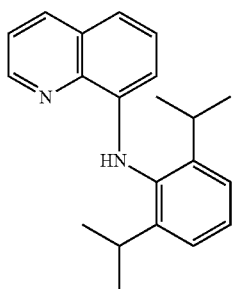

(1)

Charge a round bottomed flask equipped with a reflux condenser with tris(dibenzylidene acetone)dipalladium(0) (Pd$_2$(dba)$_3$) (0.090 mmol, Aldrich), racemic 2,2'-bis(diphenylphosphine)-1,1'-binaphthyl (rac-BINAP) (0.207 mmol; Fluka division of Aldrich), and sodium tertiary-butoxide (NaOtBu) (4.05 mmol; Aldrich) in toluene (15 mL). To the resulting suspension add 2,6-diisopropylaniline (2.88 mmol) and 8-bromoquinoline (2.88 mmol), and then heat the resulting mixture under reflux overnight. Pump down the reaction mixture to dryness under vacuum, and purify the resulting crude residue by column chromatography on silica gel eluting with 9:1 pentane:diethyl ether (C$_5$H$_{12}$:Et$_2$O) to give purified (1) in 38% yield.

$^1$H NMR (C$_6$D$_6$): 8.56 (1H, d, J=3.5 Hz, C$_9$H$_6$N); 7.92 (1H, s, NH); 7.53 (1H, d, J=8.1 Hz, C$_9$H$_6$N); 7.23-7.04 (4H, m, C$_9$H$_6$N and C$_6$(i-Pr)$_2$H$_3$); 6.79 (1H, d, J=8.1 Hz); 6.77 (1H, dd, J=8.1, 4.0 Hz, C$_9$H$_6$N); 6.35 (1H, d, J=7.5 Hz, C$_9$H$_6$N); 3.32 (2H, sp, J=6.8 Hz, CH(CH$_3$)$_2$); 1.10 (12H, br, CH(CH$_3$)$_2$). $^{13}$C{$^1$H} NMR (C$_6$D$_6$): 148.3, 147.3, 145.5, 138.4, 136.1, 135.8, 129.3, 128.1, 124.3, 121.7, 114.9, 106.5, 28.8, 24.9, 23.3.

Example 2

Preparation of
N-(2,6-dimethylphenyl)quinolin-8-amine (2)

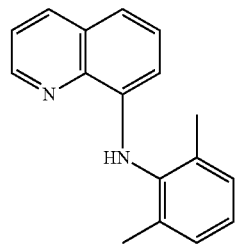

(2)

Repeat the procedure of Example 1 except use 2,6-dimethylaniline instead of 2,6-diisopropylaniline to give purified (2) in 57% yield.

$^1$H NMR (C$_6$D$_6$): 8.60 (1H, dd, J=4.0, 1.5 Hz, C$_9$H$_6$N); 7.83 (1H, s, NH); 7.59 (1H, dd, J=8.1, 1.5 Hz, C$_9$H$_6$N); 7.11 (1H, t, J=7.9 Hz, C$_9$H$_6$N); 7.03 (3H, br, C$_6$H$_3$Me$_2$); 6.92 (1H, d, J=8.1 Hz, C$_9$H$_6$N); 6.83 (1H, dd, J=8.3, 4.0 Hz, C$_9$H$_6$N); 6.35 (1H, dd, J=7.7, 0.7 Hz, C$_9$H$_6$N); 2.15 (6H, s, CH$_3$). $^{13}$C{$^1$H} NMR (C$_6$D$_6$): 147.2, 143.5, 138.7, 138.6, 137.0, 136.0, 129.3, 128.9, 128.1, 126.6, 121.5, 115.1, 106.2, 18.4.

Example 3

Preparation of
N-(2-isopropylphenyl)quinolin-8-amine (3)

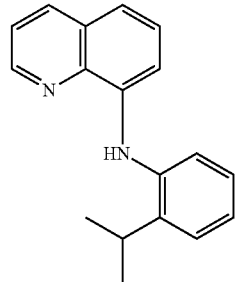

(3)

Repeat the procedure of Example 1 except use 2-isopropylaniline instead of 2,6-diisopropylaniline to give purified (3) in 73% yield.

$^1$H NMR (C$_6$D$_6$): 8.57 (1H, dd, J=4.2, 1.7 Hz, C$_9$H$_6$N); 8.37 (1H, s, NH); 7.59 (1H, dd, J=8.1, 1.3 Hz); 7.52 (1H, d, J=7.5 Hz); 7.25 (1H, dd, J=7.3, 1.3 Hz); 7.17-7.05 (m, 4H); 6.94 (1H, dd, J=7.7, 1.3 Hz); 6.83 (1H, dd, J=8.3, 4.2 Hz); (C$_9$H$_6$N and C$_6$(i-Pr)H$_4$) 3.35 (1H, sp, J=6.8 Hz, CH(CH$_3$)$_2$); 1.14 (6H, d, J=6.8 Hz, CH(CH$_3$)$_2$). $^{13}$C{$^1$H} NMR (C$_6$D$_6$): 147.4, 142.99, 142.97, 139.2, 139.1, 136.1, 129.3, 127.9, 126.8, 126.7, 124.9, 124.2, 121.7, 115.8, 107.3, 28.4, 23.3.

Example 4

Preparation of N-(2,6-dimethylphenyl)-2,4-dimethylquinolin-8-amine (4)

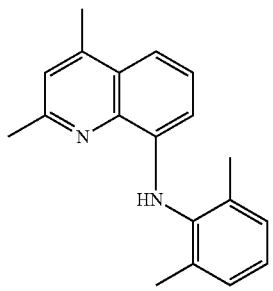

(4)

Repeat the procedure of Example 1 except use 2,6-dimethylaniline instead of 2,6-diisopropylaniline and 8-bromo-2,4-dimethylquinoline instead of 8-bromoquinoline to give purified (4) in 46% yield.

$^1$H NMR (C$_6$D$_6$): 7.95 (1H, s, NH); 7.16-7.05 (5H, m), 6.97 (1H, s), 6.41 (1H, d, J=7.3, 0.9 Hz), (C$_9$H$_4$Me$_2$N and C$_6$H$_3$Me$_2$); 2.55 (3H, s, C$_9$H$_4$(CH$_3$)$_2$N); 2.25 (3H, s, C$_9$H$_4$(CH$_3$)$_2$N); 2.21 (6H, s, C$_6$H$_3$(CH$_3$)$_2$).

Example 5

Preparation of N-(quinolin-8-yl-kappaN)-(2,6-diisopropylbenzeneaminato-kappaN)-tribenzyl-hafnium (5). [also can be named [8-(2,6-diisopropylanilido)-quinolino]hafnium tribenzyl]

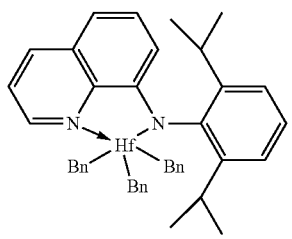

(5)

Cool a solution of N-(2,6-diisopropylphenyl)quinolin-8-amine (1) (Example 1) (1.00 mmol) in toluene (5 mL) to −20° C., and then add the cooled solution to a vial containing tetrabenzyl hafnium (Hf(Bn)$_4$) (0.95 mmol), wherein Bn is benzyl. Allow the resulting solution to warm to room temperature, and stir for 4 hours, over which time a dark orange/red color forms. Pump the reaction mixture down to dryness under vacuum, and purify the resulting crude residue by crystallization from toluene-pentane at −20° C. to give purified (5) in 76% yield.

$^1$H NMR (C$_6$D$_6$): 7.72 (1H, d, J=4.6 Hz, C$_9$H$_6$N); 7.40 (1H, d, J=8.2 Hz, C$_9$H$_6$N); 7.30 (3H, br, C$_6$(i-Pr)$_2$H$_3$); 7.06 (6H, br t, J=7.2 Hz, CH$_2$C$_6$H$_5$); 6.94 (1H, t, J=7.9 Hz, C$_9$H$_6$N); 6.81 (3H, br t, J=7.2 Hz, CH$_2$C$_6$H$_5$); 6.70 (6H, br, CH$_2$C$_6$H$_5$); 6.59 (1H, d, J=8.2 Hz, C$_9$H$_6$N); 6.44 (1H, dd, J=5.0, 7.9 Hz, C$_9$H$_6$N); 6.07 (1H, d, J=7.7 Hz, C$_9$H$_6$N); 3.31 (2H, sp, J=7.2 Hz, CH(CH$_3$)$_2$); 2.33 (6H, br s, CH$_2$Ph); 1.30 (6H, d, J=7.2 Hz, CH(CH$_3$)$_2$); 0.98 (6H, d, J=7.2 Hz, CH(CH$_3$)$_2$).

Example 6

Preparation of N-(quinolin-8-yl-kappaN)-(2,6-dimethylbenzeneaminato-kappaN)-tribenzyl-hafnium (6). [also can be named [8-(2,6-dimethylanilido)-quinolino]hafnium tribenzyl]

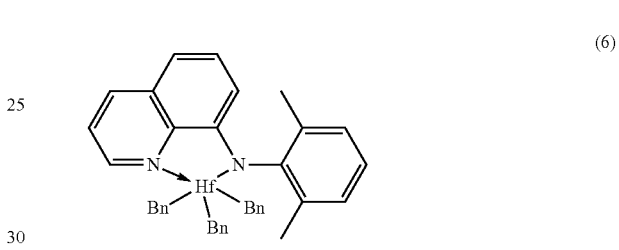

(6)

Repeat the procedure of Example 5 except use N-(2,6-dimethylphenyl)quinolin-8-amine (2) (Example 2) instead of N-(2,6-diisopropylphenyl)quinolin-8-amine (1) to give purified (6) in 66% yield.

$^1$H NMR (C$_6$D$_6$): 7.73 (1H, d, J=4.4 Hz, C$_9$H$_6$N); 7.47 (1H, d, J=7.9 Hz, C$_9$H$_6$N); 7.16 (2H, d, J=7.3 Hz, C$_6$(Me)$_2$H$_3$); 7.12 (1H, t, J=7.3 Hz, C$_6$(Me)$_2$H$_3$); 7.04 (6H, t, J=7.3 Hz, CH$_2$C$_6$H$_5$); 6.81 (3H, t, J=7.3 Hz, CH$_2$C$_6$H$_5$); 6.66 (6H, d, J=7.3 Hz, CH$_2$C$_6$H$_5$); 6.63 (1H, superimposed, C$_9$H$_6$N); 6.51 (1H, dd, J=5.0, 7.9 Hz, C$_9$H$_6$N); 6.06 (1H, d, J=7.7 Hz, C$_9$H$_6$N); 2.19 (6H, s, CH$_2$Ph); 2.09 (6H, s, C$_6$(CH$_3$)$_2$H$_3$).

Example 7

Preparation of N-(quinolin-8-yl-kappaN)-(2-isopropylbenzeneaminato-kappaN)-tribenzyl-hafnium (7). [also can be named [8-(2-isopropylanilido)-quinolino]hafnium tribenzyl]

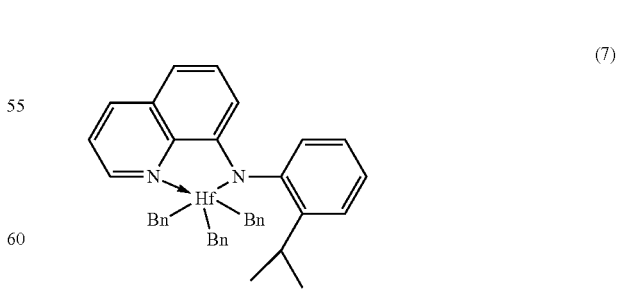

(7)

Repeat the procedure of Example 5 except use N-(2-isopropylphenyl)quinolin-8-amine (3) (Example 3) instead of N-(2,6-diisopropylphenyl)quinolin-8-amine (1) to give purified (7) in 65% yield.

¹H NMR (C₆D₆): 7.70 (1H, dd, J=4.8, 11 Hz, C₉H₆N); 7.40 (2H, m, C₉H₆N and C₆H₅(i-Pr)); 7.23 (2H, m, C₆H₅(i-Pr)); 7.04 (6H, t, J=7.9 Hz, CH₂C₆H₅); 6.95 (1H, t, J=7.9 Hz, C₆H₅(i-Pr)); 6.87 (1H, m, C₆H₅(i-Pr)); 6.79 (3H, t, J=7.9 Hz, CH₂C₆H₅); 6.69 (6H, d, J=7.9 Hz, CH₂C₆H₅); 6.59 (1H, d, J=7.9 Hz, C₉H₆N); 6.48 (1H, dd, J=4.8, 7.9 Hz, C₉H₆N); 6.07 (1H, d, J=7.7 Hz, C₉H₆N); 3.31 (1H, sp, J=7.2 Hz, CH(CH₃)₂); 2.30 (3H, d, J=12.1 Hz, C(H)(H)Ph); 2.25 (3H, d, J=12.1 Hz, C(H)(H)Ph); 1.28 (3H, d, J=7.2 Hz, CH(CH₃)₂); 1.04 (3H, d, J=7.2 Hz, CH(CH₃)₂).

Example 8

Preparation of N-(2,4-dimethylquinolin-8-yl-kappaN)-(2,6-dimethylbenzeneaminato-kappaN)-tribenzyl-hafnium (8). [also can be named [8-(2-isopropylanilido)-quinolino]hafnium tribenzyl]

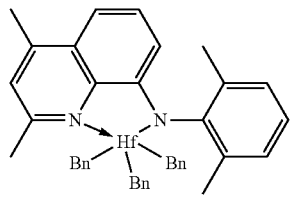

(8)

Repeat the procedure of Example 5 except use N-(2,6-dimethylphenyl)-2,4-dimethylquinolin-8-amine (4) (Example 4) instead of N-(2,6-diisopropylphenyl)quinolin-8-amine (1) to give purified (8) in 85% yield.

¹H NMR (C₆D₆): 7.19 (1H, br s, C₆(Me)₂H₃); 7.17 (2H, br s, C₆(Me)₂H₃); 7.09 (1H, dd, J=7.9, 6.8 Hz, C₉H₄Me₂N); 7.00 (1H, t, J=7.9 Hz, C₉H₄Me₂N); 6.91 (6H, br, CH₂C₆H₅); 6.81 (1H, d, J=7.9 Hz, C₉H₄Me₂N); 6.69 (3H, br, CH₂C₆H₅); 6.60 (6H, br, CH₂C₆H₅); 6.19 (1H, br t, J=4.0 Hz, C₉H₄Me₂N); 2.54 (6H, br, CH₂Ph); 2.18 (6H, s, C₆(CH₃)₂H₃); 2.00 (6H, s, C₉H₄(CH₃)(CH₃)N, superimposed).

Example 9

Preparation of [di-(8-quinolino)-amido]hafnium tribenzyl (10)

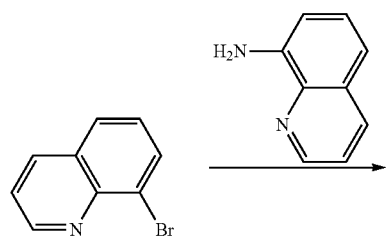

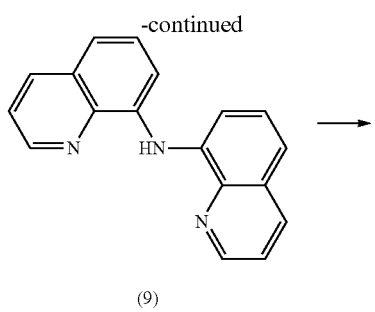

(9)

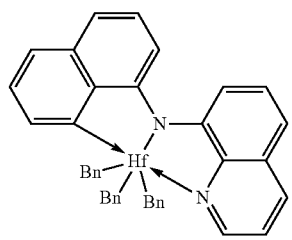

(10)

In a first reaction repeat the procedure of Example 1 except use 0.066 g, 0.072 mmol of Pd₂(dba)₃; 0.108 g, 0.173 mmol of rac-BINAP; 0.323 g, 3.36 mmol of NaOtBu; 8-aminoquinoline (0.346 g, 2.40 mmol) instead of 2,6-diisopropylaniline; 0.500 g, 2.40 mmol of 8-bromoquinoline; and 3:2 pentane:diethyl ether. Crystallize the resulting material from pentane at −20° C., yielding 94 mg (14%) of (9) as pale yellow crystals.

1H NMR (C6D6): 11.64 (1H, s, NH); 8.66 (2H, dd, J=4.0, 1.7 Hz); 7.81 (2H, d, J=7.7 Hz); 7.55 (2H, dd, J=8.3, 1.5 Hz); 7.30 (2H, t, J=8.3 Hz); 7.05 (2H, d, J=8.3 Hz); 6.77 (2H, dd, J=8.3, 4.0 Hz).

In a second reaction repeat the procedure of Example 5 except use diquinolin-8-ylamine (9) instead of N-(2,6-diisopropylphenyl)quinolin-8-amine (1) to give purified (10) in 50% yield.

¹H NMR (C₆D₆): 8.37 (2H, br d, J=4.8 Hz, (C₉H₆N)₂N); 7.53 (2H, d, J=7.9 Hz, (C₉H₆N)₂N); 7.37 (2H, d, J=8.3 Hz, (C₉H₆N)₂N); 7.17 (2H, t, superimposed, (C₉H₆N)₂N); 7.15 (6H, br, CH₂C₆H₅); 6.80 (9H, br m, CH₂C₆H₅); 6.59 (2H, dd, J=7.9, 5.0 Hz, (C₉H₆N)₂N); 6.53 (2H, t, J=6.8 Hz, (C₉H₆N)₂N); 2.28 (6H, br, CH₂Ph).

Examples A, B, C, D, E, F1 to F8, and G

Copolymerization of Ethylene and 1-octene to Give poly(ethylene 1-octene) Copolymers Follow the general procedure for copolymerization of ethylene and 1-octene described above using the metal-ligand complex (MLC) (5), (6), (7), (8) (10 times), or (10) to respectively give poly(ethylene 1-octene) copolymer (PEO) of Example A, B, C, D, E, F1 to F8, or G. Employ 145 g of ethylene in the reactions of Examples A, B, C, D, E, and G; and employ 125 g ethylene in the reactions of Examples F1 to F8. Conduct all polymerization reactions at the polymerization reaction temperature of 120° C. except conduct the polymerization reaction of Example E at the polymerization reaction temperature of 135° C. Analyze the resulting PEO copolymer using DSC and GPC as described previously. One temperature peak in DSC curves (not shown) of heat flow (Watts per gram) versus temperature (° C.) between 40° C. and 120° C., a PDI of 2.5 or less, or preferably a combination thereof, indicates compositional homogeneity. Results are shown below in Tables 1, 2a, and 2b. Normalized efficiency ratios are relative to a standard catalyst which is run at the same temperature and on the same day.

TABLE 1 certain characterizations of processes of Examples A, B, C, D, E, F1 to F8, and G employing metal-ligand complexes (5), (6), (7), (8) (ten times), and (10), respectively.

| Ex. No. | Metal-ligand complex Number | Weight of Ethylene taken up (g) | Polymerization Reaction Temperature (°C.) | Catalyst Efficiency (gPEO/ gM of MLC) | Normalized Catalyst Efficiency (to STD) |
|---|---|---|---|---|---|
| STD* | N/a | N/a | N/a | N/a | 1.0 |
| A | (5) | 33.3 | 120° C. | 125,000 | 1.5 |
| B | (6) | 43.6 | 120° C. | 162,000 | 1.8 |
| C | (7) | 26.4 | 120° C. | 74,000 | 0.7 |
| D | (8) | 24.2 | 120° C. | 180,000 | 1.8 |
| E | (8) | 34.6 | 135° C. | 155,000 | 3.1 |
| F1 | (8) | 18.6 | 120° C. | 210,000 | 2.7 |
| F2 | (8) | 14.1 | 120° C. | 158,000 | 2.1 |
| F3 | (8) | 14.2 | 120° C. | 212,000 | 2.1 |
| F4 | (8) | 22.8 | 120° C. | 128,000 | 1.8 |
| F5 | (8) | 21.1 | 120° C. | 159,000 | 1.7 |
| F6 | (8) | 20.5 | 120° C. | 115,000 | 1.6 |
| F7 | (8) | 18.5 | 120° C. | 139,000 | 1.5 |
| F8 | (8) | 21.2 | 120° C. | 118,000 | 1.7 |
| G | (10) | N/o | 120° C. | N/o | N/o |

Ex. No. = Example Number;
PEO = poly(ethylene 1-octene) copolymer;
Catalyst Efficiency (gPEO/gM of MLC) = invention catalyst efficiency calculated by dividing weight in grams of PEO product by weight in grams of metal (M) of metal-ligand complex used;
Normalized Catalyst Efficiency (to STD) is calculated by normalizing the aforementioned invention catalyst efficiency against a catalyst efficiency for a non-invention standard catalyst (*STD, not disclosed), i.e., dividing invention catalyst efficiency by the STD catalyst efficiency, wherein a normalized value of the STD catalyst efficiency is set equal to 1.0;
N/a means not applicable; and
N/o means no polymerization observed.

TABLE 2 certain characterizations of poly(ethylene 1-octene) copolymer (PEO) of Examples A, B, C, D, E, or F1 to F8 employing metal-ligand complexes (5), (6), (7), and (8) (ten times), respectively.

| Ex. No. | MLC No. | No. peaks in DSC curve | $T_m$ (°C.) | $T_c$ (°C.) | $W_{1/2(DSC)}$ (°C.) | $W_{1/2(DSC)} * T_c$ (°C.$^2$) |
|---|---|---|---|---|---|---|
| A | (5) | 1 | 95, 107 | 92 | N/a | N/a |
| B | (6) | 2 | 89, 115 | 80, 86 | N/a | N/a |
| C | (7) | 1 | 122 | 107 | N/a | N/a |
| D | (8) | 1 | 96 | 84 | N/a | N/a |
| E | (8) | 1 | 93 | 81 | N/a | N/a |
| F1 | (8) | 1 | 118 | 108 | 3.1 | 335 |
| F2 | (8) | 1 | 116 | 105 | 3.1 | 326 |
| F3 | (8) | 1 | 114 | 103 | 3.9 | 402 |
| F4 | (8) | 1 | 107 | 92 | 4.9 | 451 |
| F5 | (8) | 1 | 103 | 90 | 5.0 | 450 |
| F6 | (8) | 1 | 94 | 81 | 5.0 | 405 |
| F7 | (8) | 1 | 83 | 69 | 4.3 | 297 |
| F8 | (8) | 1 | 64 | 57 | N/a | N/a |

Ex. No. = Example Number; MLC No. = metal-ligand complex structure number; $T_m$ = melting temperature (from DSC heating curve); $T_c$ = crystallization transition temperature (from DSC cooling curve); $W_{1/2(DSC)}$ is as defined previously; * means multiplication; and N/a means not available.

TABLE 2b certain characterizations of poly(ethylene 1-octene) copolymer (PEO) of Examples A, B, C, D, E, or F1 to F8 employing metal-ligand complexes (5), (6), (7), and (8) (ten times), respectively.

| Ex. No. | MLC No. | $M_w$ (g/mol) | $M_n$ (g/mol) | PDI ($M_w/M_n$) | Octene incorporation (wt %) | Mol % vinyls ($^1$H-NMR) |
|---|---|---|---|---|---|---|
| A | (5) | 280,300 | 100,500 | 2.79 | 13.4 | 0.131 |
| B | (6) | 403,610 | 116,800 | 3.46 | 16.5 | 0.109 |
| C | (7) | 159,800 | 54,600 | 2.93 | 6.9 | 0.039 |
| D | (8) | 632,200 | 212,500 | 2.97 | 14.9 | 0.052 |
| E | (8) | 514,600 | 194,300 | 2.65 | 15.5 | 0.012 |
| F1 | (8) | 680,500 | 276,600 | 2.46 | 4.4 | 0.023 |
| F2 | (8) | 808,000 | 268,500 | 3.01 | 4.6 | 0.031 |
| F3 | (8) | 900,800 | 363,700 | 2.48 | 5.2 | 0.016 |
| F4 | (8) | 633,800 | 269,000 | 2.36 | 9.2 | 0.033 |
| F5 | (8) | 691,500 | 283,100 | 2.44 | 10.8 | 0.033 |
| F6 | (8) | 640,500 | 205,800 | 3.11 | 14.7 | 0.015 |
| F7 | (8) | 577,300 | 172,800 | 3.34 | 20.3 | 0.006 |
| F8 | (8) | 514,600 | 514,600 | 2.65 | 27.4 | 0.017 |

Ex. No. = Example Number; MLC No. = metal-ligand complex structure number; $M_w$ (g/mol) [or $M_w$ (g/mol)] = weight average molecular weight in grams per mole determined by GPC; $M_n$ (g/mol) [or $M_n$ (g/mol)] = number average molecular weight in grams per mole determined by GPC; $M_w/M_n$ = polydispersity index (PDI); Octene incorporation (wt %) means weight of 1-octene consumed divided by weight of PEO produced, expressed as a percent; Mol % vinyls ($^1$H-NMR) = mole percent of —CH═CH$_2$ remaining in the PEO as determined by proton nuclear magnetic resonance spectroscopy; and N/a means not available.

As shown by the above description, including the Examples, and data, the invention catalysts prepared from the invention metal-ligand complexes polymerizes olefin monomers (e.g., copolymerizes ethylene and 1-octene) when used in the invention process. In some embodiments the invention catalysts are characterizable as having desirable properties such as operating temperature (functioning at preferred polymerization reaction temperatures), catalyst efficiency, or a combination of any two or more thereof as described previously. This polymerization in the invention process desirably yields polyolefins. Polyolefins prepared by the process of the first embodiment are useful, among other things, as described previously, including as synthetic lubricants (synthetic motor oils) and as materials for use in manufacturing foams, films, coatings, fibers, fabrics, extruded articles, and molded articles. In some embodiments the polyolefins are characterizable as having desirable properties such as Mw, Mn, PDI, Tm, mol % vinyls, or a combination of any two or more thereof, as described previously.

While the invention has been described above according to its preferred embodiments, it can be modified within the spirit and scope of this disclosure. This application is therefore intended to cover any variations, uses, or adaptations of the instant invention using the general principles disclosed herein. Further, the instant application is intended to cover such departures from the present disclosure as come within the known or customary practice in the art to which this invention pertains and which fall within the limits of the following claims.

What is claimed is:

1. A process for polymerizing an olefin monomer, the process comprising a step of contacting together a catalytic amount of a catalyst comprising a mixture or reaction product of components (a) and (b), wherein component (a) comprises a metal-ligand complex and component (b) comprises an activating co-catalyst; and an olefin monomer as component (c);

the component (a) being one or more metal-ligand complexes of formula (I):

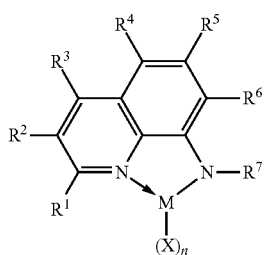
(I)

wherein:
M is a metal of Group 4 of the Periodic Table of the Elements, the metal being in a formal oxidation state of +3 or +4;
n is an integer of from 1 to 5;
each X independently is a monodentate ligand that is neutral, monoanionic, or dianionic; or two X are taken together to form a bidentate ligand that is neutral, monoanionic, or dianionic;
X and n are chosen in such a way that the metal-ligand complex of formula (I) is, in aggregate, neutral;
each of $R^1$ to $R^6$ independently is a hydrogen atom, $(C_1-C_{40})$hydrocarbyl, $(C_1-C_{40})$heterohydrocarbyl, $(C_1-C_{40})$hydrocarbyl-O—, or halogen atom;
$R^7$ independently is a $(C_1-C_{40})$hydrocarbyl or $(C_1-C_{40})$heterohydrocarbyl; or one X, when a monodentate ligand, is taken together with any one of $R^1$ to $R^7$ in such a way so that the metal-ligand complex of formula (I) contains a tridentate ligand;
each of the aforementioned hydrocarbyl and heterohydrocarbyl independently is unsubstituted or substituted with one or more substituents $R^S$; and
each $R^S$ independently is a halogen atom, polyfluoro, perfluoro, or unsubstituted $(C_1-C_{18})$alkyl, $F_3C$—, $FCH_2O$—, $F_2HCO$—, $F_3CO$—, $R_3Si$—, $RO$—, $RS$—, $RS(O)$—, $RS(O)_2$—, $R_2P$—, $R_2N$—, $R_2C=N$—, $NC$—, $RC(O)O$—, $ROC(O)$—, $RC(O)N(R)$—, or $R_2NC(O)$—, wherein each R independently is an unsubstituted $(C_1-C_{18})$alkyl; and
the component (b) being one or more activating co-catalysts, or a reaction product thereof, wherein the ratio of total number of moles of the one or more metal-ligand complexes of formula (I) to total number of moles of the one or more activating co-catalysts is from 1:10,000 to 100:1;
wherein the contacting step is performed under olefin polymerizing conditions and prepares a polyolefin, and
wherein the metal-ligand complex of formula (I) is a metal-ligand complex of formula (Ip), (Ia), (Ia-1), (Ia-1.1), or (Ia-2):

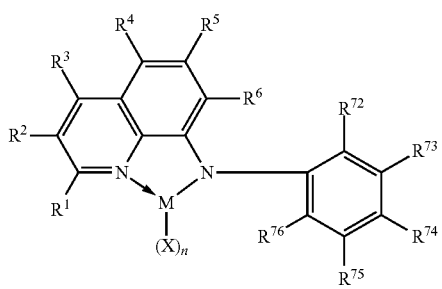
(Ip)

wherein at least one of $R^{72}$ and $R^{76}$ independently is a $(C_1-C_{40})$alkyl and each of the remainder of $R^{72}$ to $R^{76}$ independently is a hydrogen atom or $R^S$;

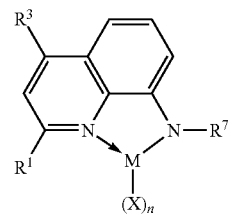
(Ia)

wherein in formula (Ia) each of $R^1$ and $R^3$ independently is a $(C_1-C_{40})$hydrocarbyl or $(C_1-C_{40})$heterohydrocarbyl;

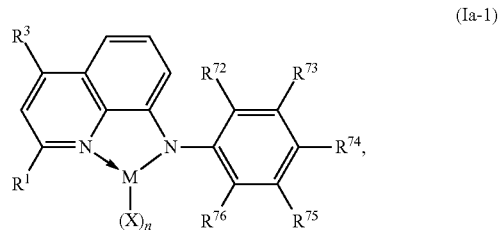
(Ia-1)

wherein in formula (Ia-1) each of $R^{72}$ to $R^{76}$ independently is a hydrogen atom, a $(C_1-C_{40})$alkyl, or $R^S$, wherein $R^S$ is as defined previously, and wherein in formula (Ia-1) each of $R^1$ and $R^3$ independently is a $(C_1-C_{40})$hydrocarbyl or $(C_1-C_{40})$heterohydrocarbyl;
or

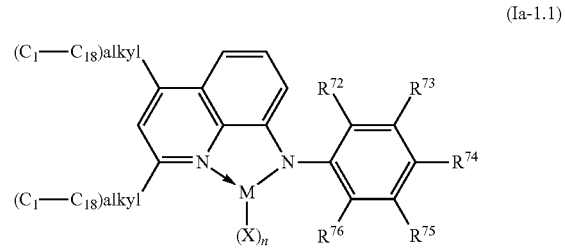
(Ia-1.1)

wherein in formula (Ia-1.1) each of $R^{72}$ to $R^{76}$ independently is a hydrogen atom, a $(C_1-C_{40})$alkyl, or $R^S$, wherein $R^S$ is as defined previously; or

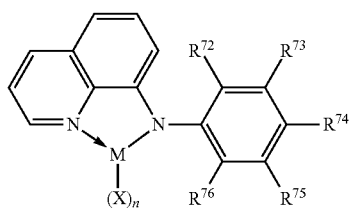
(Ia-1.2)

wherein in formula (Ia-1.2) each of $R^{72}$ to $R^{76}$ independently is a hydrogen atom, a $(C_1-C_{40})$alkyl, or $R^S$, wherein $R^S$ is as defined previously.

2. The process as in claim 1, wherein the metal-ligand complex of formula (I) is characterized by any one or more of limitations (a) to (l):
(a) M is hafnium;
(b) n is 3 and each X is a monodentate ligand that is a monoanionic ligand;
(c) at least $R^1$ is $(C_1-C_{40})$hydrocarbyl;
(d) $R^7$ is a substituted $(C_6-C_{40})$aryl;
(e) at least $R^3$ is $(C_1-C_{40})$hydrocarbyl;

(f) the catalyst is characterized by a catalyst efficiency of at least 130,000 grams of the polyolefin per gram of metal (M) of the metal-ligand complex of formula (I);

(g) the polyolefin is a poly(ethylene alpha-olefin) copolymer characterized by a differential scanning calorimetry crystallization transition temperature ($T_c$) of 60° C. or higher; heat flow versus temperature cooling and heating curves independently exhibiting single peaks for both crystallization and melting transitions, respectively; and either (i) a full width at half maximum peak height in degrees Celsius ($W_{1/2(DSC)}$) corresponding to a crystallization transition from the DSC cooling curve of less than 5.0° C. or (ii) a multiplication product of $T_c * W_{1/2 (DSC)}$ that is less than 500° C. squared;

(h) the polyolefin is a poly(ethylene alpha-olefin) copolymer characterized by a polydispersity index of less than 3.0;

(i) the polyolefin is a poly(ethylene alpha-olefin) copolymer characterized by a $^1$H NMR spectroscopy by a mole percent of vinyl groups, expressed as —CH=CH$_2$ groups per 1000 carbon atoms of the polyolefin, of less than 0.10 mole percent;

(j) the polyolefin is a poly(ethylene alpha-olefin) copolymer characterized by a weight average molecular weight of at least 500,000 grams per mole as determined by gel permeation chromatography;

(k) the polyolefin is a poly(ethylene alpha-olefin) copolymer characterized by a number average molecular weight of at least 170,000 grams per mole as determined by gel permeation chromatography; and (l) the process is performed at a reaction temperature of at least 140° C. and less than 300° C.

3. The process as in claim 2, the process being characterized by at least each of limitations (a) to (c) and limitation (d); or the process being characterized by at least each of limitations (a) to (c) and limitation (e) and, optionally, limitation (d); or the process being characterized by at least each of limitations (a) to (c) and limitation (f) and, optionally, limitation (d) or (e), or limitations (d) and (e); or the process being characterized by at least each of limitations (a) to (c) and limitation (g) and, optionally, limitation (d), (e), or (f) or limitations (d), (e) and (f); or the process being characterized by at least each of limitations (a) to (c) and limitation (h) and, optionally, limitation (d), (e), (f), or (g) or limitations (d), (e), (f) and (g); or the process being characterized by at least each of limitations (a) to (c) and limitation (i) and, optionally, limitation (d), (e), (f), (g), or (h) or limitations (d), (e), (f), (g) and (h); or the process being characterized by at least each of limitations (a) to (c) and limitation (j) and, optionally, limitation (d), (e), (f), (g), (h), or (i) or limitations (d), (e), (f), (g), (h) and (i); or the process being characterized by at least each of limitations (a) to (c) and limitation (k) and, optionally, limitation (d), (e), (f), (g), (h), (i), or (j) or limitations (d), (e), (f), (g), (h), (i) and (j); or the process being characterized by at least each of limitations (a) to (c) and limitation (k) and, optionally, limitation (d), (e), (f), (g), (h), (i), (j), or (k) or limitations (d), (e), (f), (g), (h), (i), (j) and (k); or the process being characterized by at least each of limitations (a) to (c) and limitation (k) and, optionally, limitation (d), (e), (f), (g), (h), (i), (j), (k), or (l) or limitations (d), (e), (f), (g), (h), (i), (j), (k) and (l).

4. The process as in claim 2 or 3, wherein the polyolefin is a poly(ethylene alpha-olefin) copolymer, the poly(ethylene alpha-olefin) copolymer being characterized by at least a combination comprising a polydispersity index of less than 3.0; single peaks observed in both the DSC heating and cooling curves; and $W_{1/2(DSC)}$ less than 5.0° C.; or wherein the polyolefin is a poly(ethylene alpha-olefin) copolymer, the poly(ethylene alpha-olefin) copolymer is characterized by at least a combination comprising a polydispersity index of less than 2.5; $W_{1/2(DSC)}$ less than 4.0° C.; and the mole percent vinyl groups is less than 0.03 mole percent; or wherein the polyolefin is a poly(ethylene alpha-olefin) copolymer, the poly(ethylene alpha-olefin) copolymer is characterized by at least a combination comprising a polydispersity index of less than 3.0; single peaks observed in both the DSC heating and cooling curves; and $T_c * W_{1/2(DSC)}$ less than 500° C. squared; or wherein the polyolefin is a poly(ethylene alpha-olefin) copolymer, the poly(ethylene alpha-olefin) copolymer is characterized by at least a combination comprising a polydispersity index of less than 2.5; $T_c * W_{1/2(DSC)}$ less than 400° C. squared; and the mole percent vinyl groups is less than 0.03 mole percent.

5. The process as in claim 4, wherein the catalyst is characterized by a catalyst efficiency of at least 200,000 grams of the polyolefin per gram of metal (M) of the metal-ligand complex of formula (I).

6. The process as in claim 1, wherein in the metal-ligand complex of formula (Ip) $R^1$ is ($C_1$-$C_{40}$)hydrocarbyl, ($C_1$-$C_{40}$)heterohydrocarbyl, ($C_1$-$C_{40}$)hydrocarbyl-O—, or halogen atom.

7. The process as in claim 1, wherein the metal-ligand complex is metal-ligand complex (8):

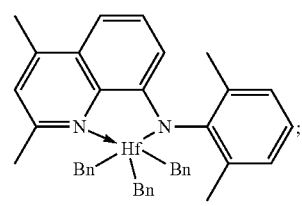

(8)

or any one of metal-ligand complexes (5) to (7) and (10):

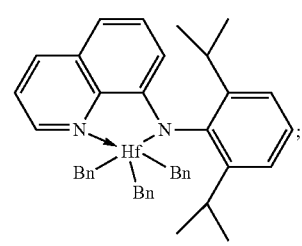

(5)

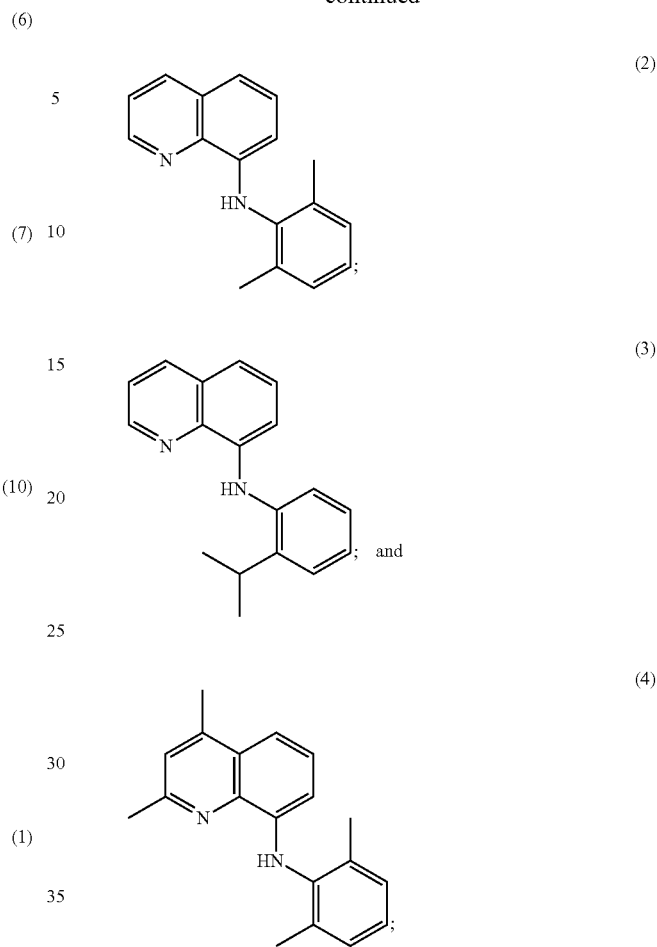
8. A ligand of any one of formulas (1) to (4):
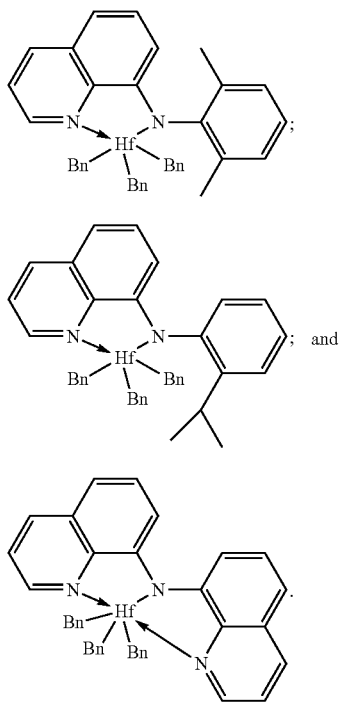
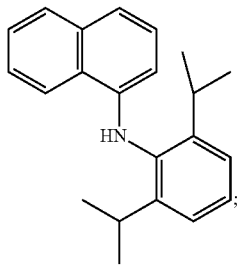
or a Group 1 or 2 metal salt thereof.
9. A metal complex comprising the ligand of claim 8.
10. A catalyst comprising the metal complex of claim 9.
* * * * *